US008276587B2

(12) United States Patent
Zhang et al.

(10) Patent No.: US 8,276,587 B2
(45) Date of Patent: Oct. 2, 2012

(54) AUTOMATED QUALITATIVE MASK FIT TESTER

(75) Inventors: Hai Zhang, Plymouth, MN (US); Will Zanto, Blaine, MN (US); Qian Shi, Blaine, MN (US); Greg Olson, Shoreview, MN (US); Phillip Poeschl, Maplewood, MN (US); Vincent Majkowski, Maple Grove, MN (US); Stuart J. Olstad, Plymouth, MN (US)

(73) Assignee: TSI, Incorporated, Shoreview, MN (US)

( * ) Notice: Subject to any disclaimer, the term of this patent is extended or adjusted under 35 U.S.C. 154(b) by 665 days.

(21) Appl. No.: 12/372,082

(22) Filed: Feb. 17, 2009

(65) Prior Publication Data
US 2009/0209877 A1 Aug. 20, 2009

Related U.S. Application Data

(60) Provisional application No. 61/029,119, filed on Feb. 15, 2008, provisional application No. 61/052,882, filed on May 13, 2008, provisional application No. 61/146,482, filed on Jan. 22, 2009.

(51) Int. Cl.
*A61M 16/00* (2006.01)
*A61M 16/14* (2006.01)
*A61M 15/00* (2006.01)
(52) U.S. Cl. ......... 128/206.21; 128/203.19; 128/204.24; 128/204.25; 128/205.25; 128/206.26; 239/338
(58) Field of Classification Search ............. 128/200.14, 128/200.18, 200.21, 200.23, 202.27, 202.12, 128/203.21, 203.24, 203.27, 204.17, 204.18, 128/204.21, 204.22, 204.24, 206.24; 239/338
See application file for complete search history.

(56) References Cited

U.S. PATENT DOCUMENTS
2,421,359 A 5/1947 Sutherland
(Continued)

FOREIGN PATENT DOCUMENTS
JP 2002-17662 1/2002
(Continued)

OTHER PUBLICATIONS

Omron, "COMP Elite, Compact Compressor Nebulizer, Model NE-C30, Instruction Manuel," (2006), Japan.
(Continued)

*Primary Examiner* — Justine Yu
*Assistant Examiner* — Clinton T Ostrup
(74) *Attorney, Agent, or Firm* — Patterson Thuente Christensen Pedersen, P.A.

(57) ABSTRACT

A hand-held, automated qualitative fit tester (QLFT) for establishing gas mask fit integrity. The automated QLFT may be configured to utilize a pressure source in combination with a cartridge and a nebulizer to generate aerosols having size distributions and concentrations that are substantially the same as OSHA-approved manual units. The QLFT may further include a cartridge that contains the aerosol solution used to test mask integrity. The cartridge may be configured to recapture solution that collects on the interior walls of the nebulizer. The automated QLFT may also be equipped with a microprocessor for executing sequences that are in substantive compliance with 29 CFR 1910.134 and for writing to a data storage device. The automated aspects of the invention can reduce or negate the need for operating personnel to repeatedly and manually actuate a squeeze ball and record results manually, as is required with present OSHA-approved hand-held aerosol generators.

17 Claims, 19 Drawing Sheets

U.S. PATENT DOCUMENTS

| | | | |
|---|---|---|---|
| 2,605,764 | A | 8/1952 | Adams et al. |
| 3,018,971 | A * | 1/1962 | Cheney .................. 239/338 |
| 3,097,645 | A | 7/1963 | Lester |
| 3,172,406 | A | 3/1965 | Bird et al. |
| 3,695,516 | A * | 10/1972 | Rogers .................. 239/135 |
| 4,007,238 | A | 2/1977 | Glenn |
| 4,195,044 | A | 3/1980 | Miller |
| 4,731,520 | A | 3/1988 | Glucksman et al. |
| 4,846,166 | A | 7/1989 | Willeke |
| 4,877,989 | A | 10/1989 | Drews et al. |
| RE33,717 | E | 10/1991 | Svoboda |
| 5,156,776 | A | 10/1992 | Loedding et al. |
| 5,221,935 | A | 6/1993 | Uzita |
| 5,241,954 | A * | 9/1993 | Glenn .................. 128/200.18 |
| 5,299,565 | A | 4/1994 | Brown |
| 5,490,630 | A | 2/1996 | Hecker |
| 5,549,102 | A | 8/1996 | Lintl et al. |
| 5,752,054 | A | 5/1998 | Garber et al. |
| 5,755,218 | A | 5/1998 | Johansson et al. |
| 5,875,934 | A | 3/1999 | Miller et al. |
| 5,893,070 | A | 4/1999 | Garber et al. |
| 6,009,869 | A | 1/2000 | Corbeil |
| 6,085,055 | A | 7/2000 | Shin et al. |
| 6,241,218 | B1 | 6/2001 | Tanitomi |
| 6,318,360 | B1 | 11/2001 | Attolini |
| 6,435,009 | B1 | 8/2002 | Tilley |
| 6,619,284 | B2 | 9/2003 | Kong |
| 6,637,430 | B1 | 10/2003 | Voges et al. |
| 6,698,421 | B2 | 3/2004 | Attolini |
| 6,729,327 | B2 | 5/2004 | McFarland, Jr. |
| 6,796,513 | B2 | 9/2004 | Fraccaroli |
| 6,851,626 | B2 | 2/2005 | Patel et al. |
| 6,883,517 | B2 | 4/2005 | Halamish |
| 6,955,170 | B1 | 10/2005 | Mullins et al. |
| 7,040,549 | B2 | 5/2006 | Ivri et al. |
| 7,164,879 | B2 | 1/2007 | Benner et al. |
| 7,191,777 | B2 | 3/2007 | Brand et al. |
| 7,195,011 | B2 | 3/2007 | Loeffler et al. |
| 7,267,120 | B2 | 9/2007 | Rustad et al. |
| 7,360,536 | B2 | 4/2008 | Patel et al. |
| 7,461,655 | B2 | 12/2008 | Sexton et al. |
| 2003/0004470 | A1 | 1/2003 | Hickerson et al. |
| 2003/0205229 | A1* | 11/2003 | Crockford et al. ....... 128/204.23 |
| 2004/0004133 | A1 | 1/2004 | Ivri et al. |
| 2004/0031485 | A1 | 2/2004 | Rustad et al. |
| 2004/0210151 | A1* | 10/2004 | Tsukashima et al. ......... 600/532 |
| 2006/0201501 | A1* | 9/2006 | Morrison et al. ....... 128/203.27 |
| 2007/0076067 | A1* | 4/2007 | Hamano et al. .................. 347/86 |
| 2008/0202627 | A1 | 8/2008 | Mas et al. |
| 2008/0236305 | A1 | 10/2008 | Masset et al. |
| 2008/0283050 | A1* | 11/2008 | Faram ..................... 128/200.21 |

FOREIGN PATENT DOCUMENTS

| | | |
|---|---|---|
| WO | WO 91-16937 | 11/1991 |

OTHER PUBLICATIONS

Pari, "Trek S, Compact Nebulizer System, Instructions for Use," (2008), Virginia.

3M, "Qualitative Fit Test Apparatus FT-10 (Sweet) and FT-30 (Bitter) Instructions for Use," (2005), Minnesota.

Chan et al. "Output Characteristics of DeVilbiss No. 40 hand-held jet nebulizers," Eur. Respr J. (1990), pp. 1197-1201.

Fairfax, U.S. Department of Labor, Occupational Safety & Health Administration, "Standard Interpretations , Use of Multi-Station electric pump nebulizer and the squeeze bulb Bitrex for QLIFT," (2001).

Moldex, "EZ Touch Powered Nebulizer, a Rapid Fit Testing Solution," product believed to be sold by Moldex prior to Feb. 2008.

Lin, Department of Health and Human Services, "letter Re K070990, dated May 18, 2007," (2007).

Apex, "AC/DC Bettery Portable Compressor Nebulizer," (2006), Taiwan.

National Jewish Medical and Research Center, Standard Operating Procedure, "Qualitative Fit Testing Procedure Using the DeVilbiss Nebulizer Device," published prior to Feb. 2008.

Fairfax, Director of Compliance Programs, "letter to Lee S. Newman, M.D., MA, dated May 9, 2000," (2000), Washington, D.C.

"Qualitative Fit Testing Device, Brochure" (2007).

Fairfax, Director of Enforcement Programs, "letter, dated Mar. 8, 2001, re: use of multi-station electric pump nebulizer and the squeeze bulb Bitrex for QLFT,"(2001), Washington, D.C.

Moldex, "Accessories, EZ Touch Powered Nebulizer," (2009).

International Search Report and the Written Opinion (PCT/US2009/034292), dated Jan. 14, 2011.

Photographs A1-A5 of Mobineb portable compressor nebulizer, manufactured by Apex Medical Corportation, Taipei County, Taiwan, device sold prior to Feb. 17, 2009.

International Search Report and the Written Opinion of the International Searching Authority (PCT/US2009/034292), dated Jan. 14, 2011.

\* cited by examiner

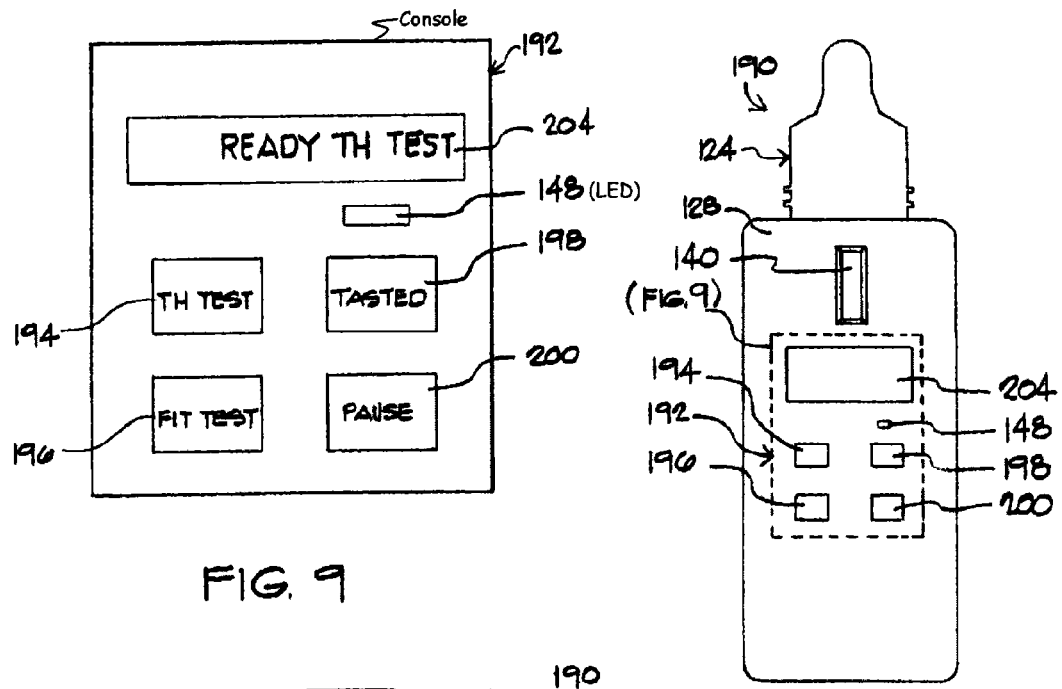
FIG. 9
FIG. 8
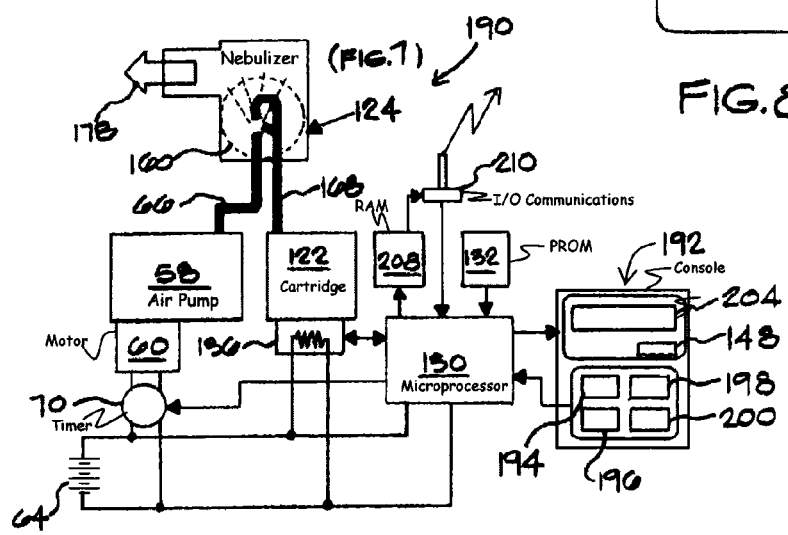
FIG. 10

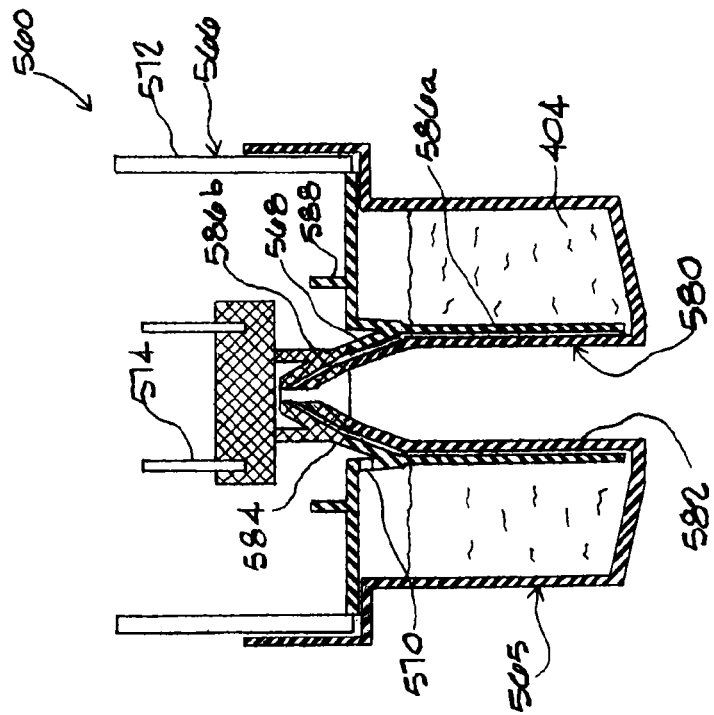
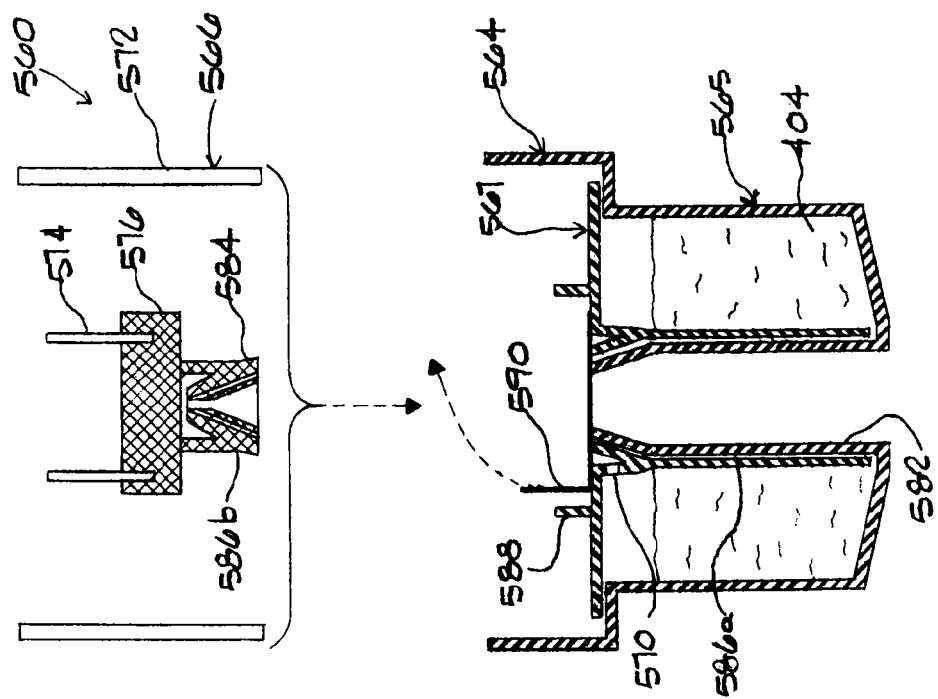
FIG. 20A
FIG. 20B

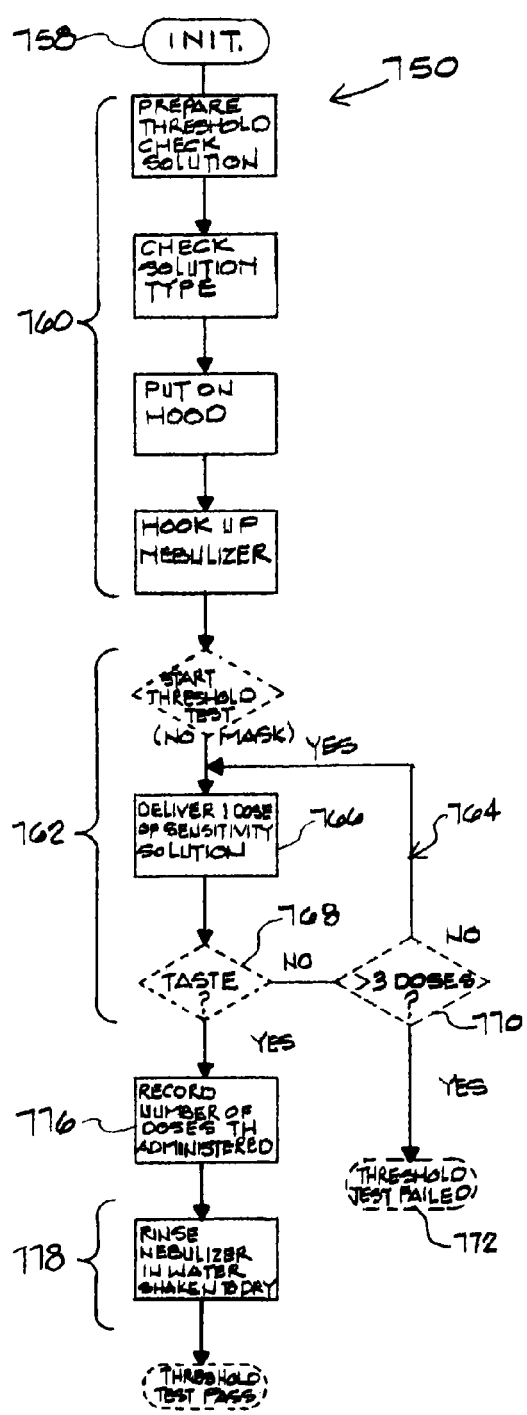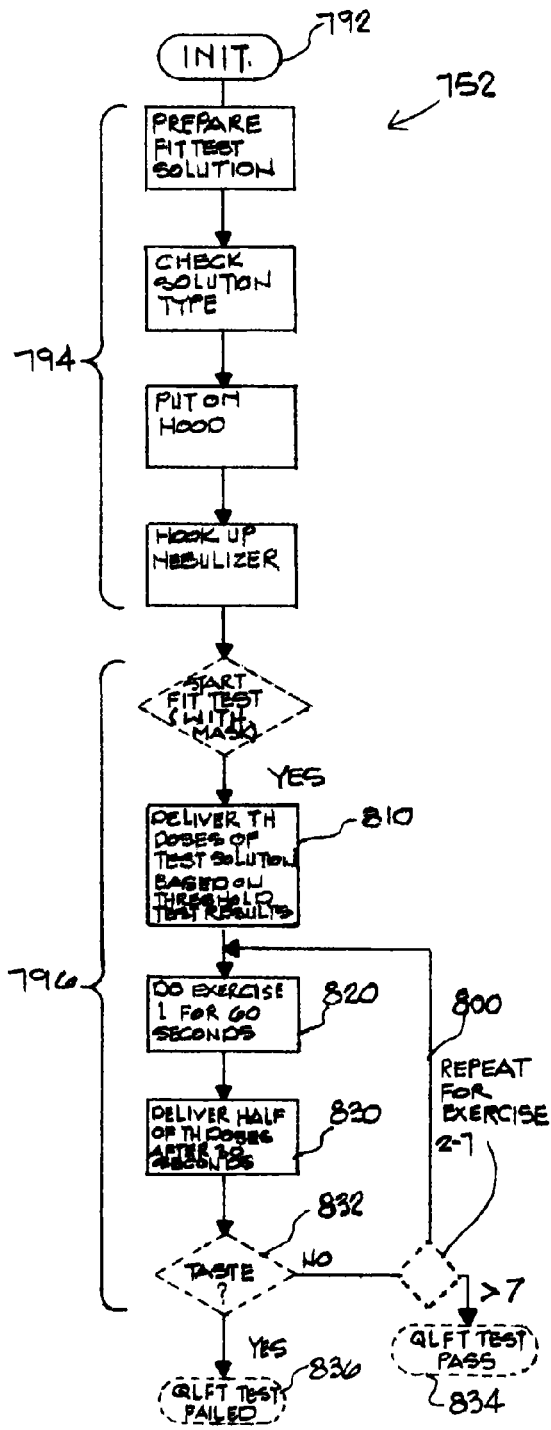
FIG. 26                    FIG. 27

AUTOMATED QUALITATIVE MASK FIT TESTER

RELATED APPLICATIONS

The present application claims the benefit of U.S. Provisional Application No. 61/029,119, filed Feb. 15, 2008, U.S. Provisional Application No. 61/052,882, filed May 13, 2008, and U.S. Provisional Application No. 61/146,482, filed Jan. 22, 2009, all of which are hereby incorporated by reference in their entirety.

FIELD OF THE INVENTION

The present disclosure relates generally to the field of mask and respirator fit testing, and more specifically to an apparatus and method for a hand-held automated aerosol generator for fit testing.

BACKGROUND OF THE INVENTION

Qualitative fit testers (QLFT) may be used to test the integrity of a gas mask and the fit of the mask to a specific individual. Such testers are "qualitative" in the sense that they do not quantify the size of a leak, but merely that the leak is present. Generally, the mask is fitted on the individual and an aerosol of a solution having a distinct flavor is caused to flow against the mask and the fitted seal between the mask and the individual. If the individual can taste the distinct flavor of the solution with the mask on, the mask is known to leak, likely around the fitted seal. Adjustments are made and the test repeated until the individual can no longer detect the aerosol solution.

Qualitative fit testing requires the participation of the individual being fitted. The sensitivity of individuals to a particular testing solution may vary. Accordingly, the fit testing is often preceded by a threshold test to assess the sensitivity of the individual to the flavored aerosol solution so that a proper dose can be determined for the fit test. The threshold test is usually conducted without a mask on the individual. Because of the absence of a mask during the threshold test, the aerosol solution for the threshold test is often a diluted version of the aerosol solution used in the fit test.

The United States Department of Labor, or more specifically the Occupational Safety and Health Administration (OSHA), has promulgated accepted fit testing protocols for qualitative fit testing, codified at 29 CFR 1910.134 (hereinafter "OSHA standards"), which is incorporated by reference herein except for express definitions that may be included therein. The OSHA standards include guidelines for the use of aerosol solutions containing saccharin or Bitrex® (BITREX). Saccharin is an artificial sweetener comprising benzoic sulfinide. BITREX is a bittering agent comprising denatonium benzoate, the name being a registered trademark of Johnson Matthey Public Limited Co., United Kingdom. The OSHA standards also include guidelines for mixing aerosol solutions for threshold testing and fit testing.

Current hand-held QLFT aerosol generators utilize a squeeze ball pressure generator operatively coupled with a nebulizer to deliver aerosols during a qualitative fit test. The squeeze ball is actuated manually by testing personnel. A single qualitative fit test may require in excess of 250 actuations of the squeeze ball pressure generator. Testing personnel may test several individuals in a single day, requiring actuation of the squeeze ball pressure generator thousands of times in the course of a full day of qualitative fit testing.

The squeeze ball pressure generator is known to produce concentrations and size distributions that vary substantially. Chan et al. documents the output characteristics of the DEVILBISS 40, a nebulizer that has been widely used for QLFT applications. See Chan, K. N., M. M. Clay and M. Silverman, "Output Characteristics of DeVilbiss No. 40 Hand Held jet Nebulizers," Eur Respir J, 1990, 3, 1197-1201, which is hereby incorporated by reference except for definitions explicitly defined therein. Chan reports a variation in mass concentration from 14.3-mg to 30.7-mg saline and variation in the median diameter of aerosol droplets from about 6- to 12-micrometers (µm). The variations can stem from non-repeatability of generated actuation pressures, particularly between different test operators. Assuming median levels midway between the minimum and maximum concentrations/aerosol droplet sizes (i.e. 22.5-mg concentration and 9 µm aerosol droplet size), the non-repeatability from median is about ±36% for the concentration and ±3-µm for the aerosol droplet size.

The FT-13, distributed by 3M, Minnesota, USA, is a standard QLFT nebulizer on the market intended to be an equivalent of the DEVILBISS 40. The FT-13 includes a reservoir for holding about 5 cubic centimeters (cc) of aerosol solution. The size of the reservoir requires refilling the reservoir after a limited number of qualitative fit tests. Moreover, the orientation of many current hand-held QLFT aerosol generators must be maintained in a substantially vertical orientation when aerosol solution is in the reservoir, lest the aerosol solution be spilled out of the nebulizer. Existing nebulizers are also prone to clogging when certain aerosol solutions, such as saccharin, are utilized.

Testing personnel must also keep track of the number of squeezes during the entirety of the test in order to comply with the OSHA standard. Test results are typically manually written after each qualitative fit test.

Given the inconveniences and variations associated with present fit testing apparatuses and procedures, an improved system that substantively complies with OSHA-accepted fit testing protocol is welcome.

SUMMARY OF THE INVENTION

The various embodiments of the invention include a hand-held, automated QLFT aerosol generator that relieves operating personnel of the need to actuate a squeeze ball pressure generator while providing a reservoir that is substantially larger (on the order of five times greater volume) and more readily refilled than with current hand-held QLFT aerosol generators. Some embodiments can also automatically execute the protocol of the OSHA standard and store the results.

The various embodiments of the automated QLFT aerosol generator utilize a pressure source such as an electric powered pump or blower a pressurized gas canister or an air compressor to deliver a pressurized air stream to a nebulizer unit. The pressure source and delivery plumbing may be sized and calibrated to deliver substantially the same aerosol concentrations and size distributions as the hand-held QLFT aerosol generators that comply with the OSHA standard.

In some embodiments, a cartridge-type reservoir is coupled to the nebulizer unit to provide aerosol solution. The cartridge may be heated to maintain the viscosity of certain aerosol solutions at values that mitigate against the fouling of the nebulizer unit. Alternatively or in addition, a flow impactor may be configured to prevent clogging of the nebulizer unit. The cartridge may be designed to cooperate with the nebulizer unit to recaptures aspirated aerosol solution that collects on the interior surfaces of the nebulizer unit and routes it back into the cartridge for reuse. The cartridge, which may be refillable or non-refillable, may also comprise a removable cap and/or seal that seals the cartridge to prevent spillage or evaporation of the aerosol solution during shipping, handling and storage. The pressure source and heater may be powered from an AC power source and/or from batteries.

A microprocessor may be incorporated that executes a sequence or sequences of instructions from firmware and writes data from the fit test to random access memory. Various instruction sequences may be initiated by the push of a button and cause the automated QLFT aerosol generator to automatically execute a test that is in substantive compliance with the OSHA standard. The microprocessor may be operatively coupled with a display to prompt the operator to do certain steps in the test sequence and to advise the operator of the status and/or test sequence being executed by the unit.

BRIEF DESCRIPTION OF THE DRAWINGS

FIG. 8 is a rear elevation view of a hand-held, automated QLFT aerosol generator according to an embodiment of the invention;

FIG. 9 is an inset view of the control interface of the automated QLFT aerosol generator of FIG. 8;

FIG. 10 is a block schematic diagram of the automated QLFT aerosol generator of FIG. 8;

FIG. 20A is a partial sectional view of a cartridge and removable housing assembly prior to assembly in an embodiment of the invention;

FIG. 20B is a partial sectional view of the cartridge and removable housing assembly of FIG. 20A;

FIG. 26 is a flow diagram of a threshold sensitivity test in an embodiment of the invention; and FIG. 27 is flow diagram of a fit test in an embodiment of the invention.

DETAILED DESCRIPTION OF CERTAIN EMBODIMENTS

Figure 1:
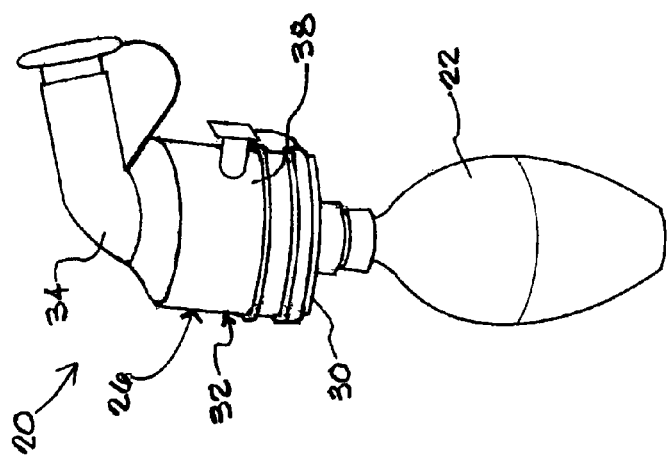
FIG. 1 is a perspective view of a hand-held QLFT aerosol generator utilizing a manual squeeze ball pressure generator.
Figure 5:
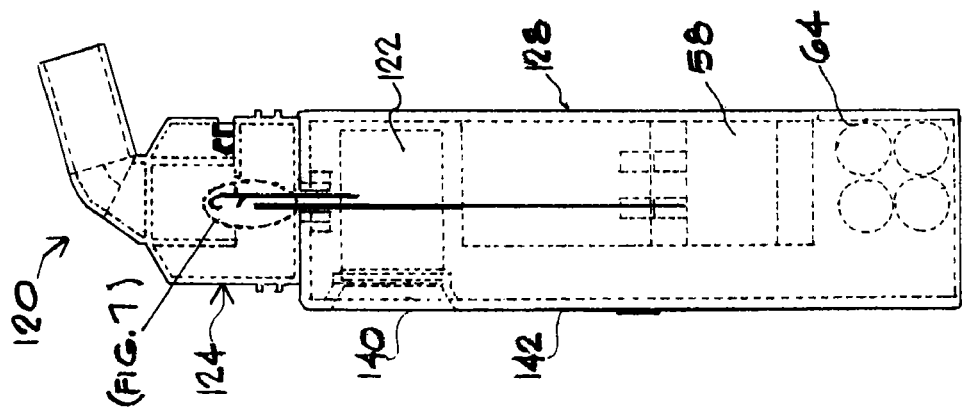
FIG. 5 is a side elevation view of the automated QLFT aerosol generator of FIG. 3.
Figure 4:
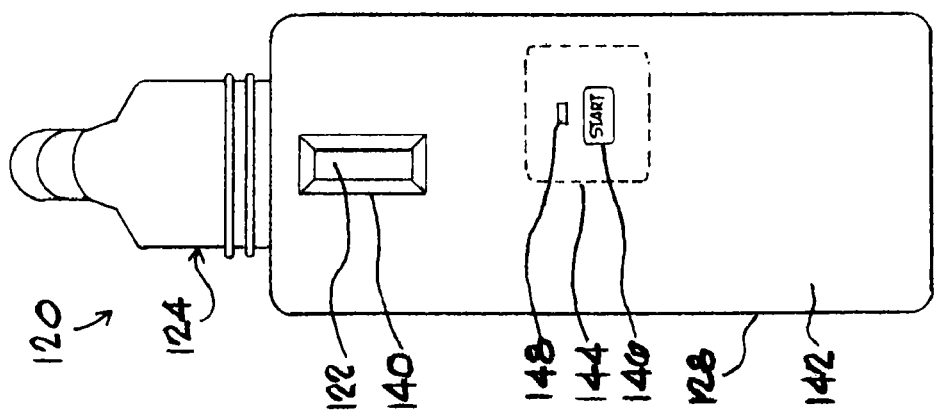
FIG. 4 is a rear elevation view of the automated QLFT aerosol generator of FIG. 3.
Figure 3:
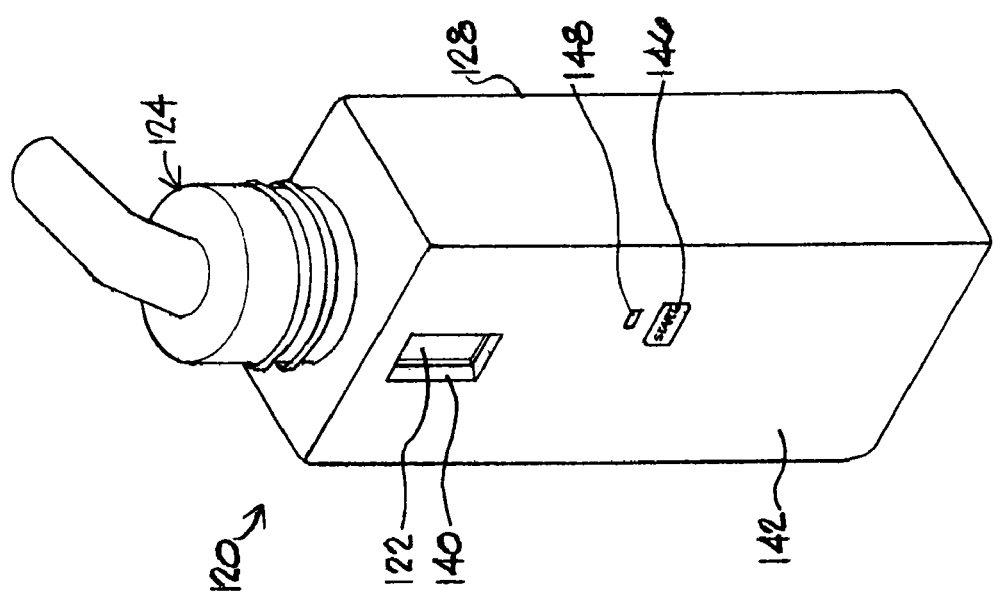
FIG. 3 is perspective view of a hand-held, automated QLFT aerosol generator according to an embodiment of the invention.

Referring to FIG. 1, a hand-held manual qualitative fit tester (QLFT) aerosol generator 20 is depicted. The manual QLFT aerosol generator 20 comprises a squeeze ball pressure generator 22 in fluid communication with a nebulizer unit 26. The nebulizer unit 26 includes a basin 30 and an upper housing 32 having an exhaust port 34. The basin 30 and upper housing 32 are threadably engaged to form a chamber 38. A seal is maintained between the basin 30 and the upper housing 32 with an o-ring. The basin 30 typically holds about 5 cubic centimeters (cc) of aerosol solution.

In operation, an operator manually squeezes the ball of the squeeze ball pressure generator 22, which forces air through a nozzle (not depicted in FIG. 1) and entrains aerosol solution from the basin 30 into the air stream exiting the nozzle to form an aerosol that exits the exhaust port 34. To create a desired concentration level of aerosol, the operator typically has to actuate the squeeze ball pressure generator 22 in rapid succession a number of times. The OSHA-accepted fit testing protocols for QLFT (29 CFR 1910.134) calls for successive squeezes of the squeeze ball in increments of 10 squeezes.

When the basin 30 contains aerosol solution, the nebulizer unit 26 should be maintained in a substantially upright position (i.e. with the basin 30 facing substantially upward). If laid on its side, the aerosol solution in the basin 30 can run out of the exhaust port 34. Structurally, the manual QLFT aerosol generator 20 is not amenable to a vertical orientation.

To refill the nebulizer unit 26, the upper housing 32 is unthreaded from the basin 30, aerosol solution placed into the basin, and the housing 32 rethreaded onto the basin 30. The threading and rethreading operations are time consuming, often done while a test is under way and while individual under test waits. The shallow pitch of the basin 30 makes it easy to tip during this operation, particularly when the operator wishes to fill the nebulizer unit to the maximum extent to reduce the number of refilling operations performed over the course of a work day.

Figure 2:
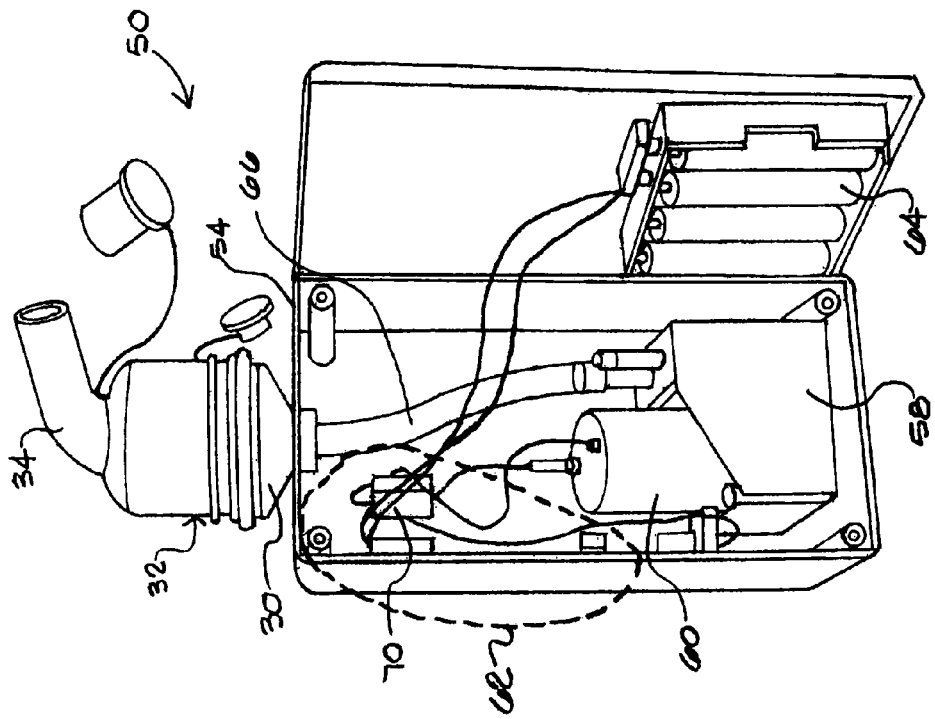
FIG. 2 is perspective view of a hand-held, automated QLFT aerosol generator according to an embodiment of the invention.

Referring to FIG. 2, an automated QLFT aerosol generator 50 is depicted in an embodiment of the invention. The automated QLFT aerosol generator 50 includes the nebulizer unit 26 mounted on a hand-held console box 54. The console box 54 may contain a pressure source such as an air pump 58 powered by an electric motor 60, control circuitry 62, and a power source 64 such as the batteries depicted. An air line 66 may provide fluid communication between the air pump 58 and the nebulizer unit 26. The control circuitry 62 may include a timer 70.

In operation, the timer 70 may be activated to energize the air pump 58 for a preset interval of time. The interval of time may be adjusted so that the mass of aerosol solution atomized by the nebulizer unit 26 over the time interval is equal to the mass produced by a predetermined equivalent number of activations of the manual QLFT aerosol generator 20. For example, 10 activations (squeezes) of the squeeze ball pressure generator 22 may be known to consume a certain mass of a certain aerosol solution. The air pump 58 may be run for a set amount of time so that the mass consumption is the same as for the 10 activations. As an alternative to measuring the mass consumed, other techniques may be used such as a volumetric measurement or a measurement of the aerosol solution agent instead of the mixed aerosol solution.

Referring to FIGS. 3 through 7, an automated QLFT aerosol generator 120 including a quick connecting solution cartridge 122 for dispensing aerosol solution into a nebulizer unit 124 is depicted in an embodiment of the invention. The automated QLFT aerosol generator 120 includes a console box 128 that may house and comprise many of the same components as the rendition of FIG. 2, such as the air pump 58, the electric motor 60, the air line 66, the control circuitry 62, the power source 64 and the timer 70. In addition, the console box 128 may include a microprocessor 130 operatively coupled to a memory device such as a programmable read-only memory (PROM) 132. Remote control of the microprocessor 130 may be accomplished via a communications port 134 (FIG. 6) accessible from the exterior of the console box 128. A heater 136 may be operatively coupled to the solution cartridge 122.

The exterior of the console box 128 may include a cartridge portal 140 that may be accessed from a rear face 142 of the console box 128. The rear face 142 may further include an operator interface 144 comprising a start button 146 and an LED indicator light 148.

Functionally, the quick connecting solution cartridge 122 enables an operator to quickly and cleanly recharge the automated QLFT aerosol generator 120 with aerosol solution. The cartridge portal 140 permits access from outside the unit for faster and easier operation. Also, the cartridge may be sized to contain a substantially greater volume of aerosol solution than the basin 30 of the manual QLFT aerosol generator 20. For example, a cartridge may be sized to contain 25-cc of aerosol solution, which is on the order of five times greater than existing basin designs.

In operation, an operator pushes the start button 146, which can trigger the microprocessor 130 to access and execute a sequence of microprocessor-readable instructions recorded in the PROM 132. The sequence may include timed switching of the air pump 58, or initiate the timer 70 to accomplish the same function. The microprocessor 130 may illuminate the LED indicator light 148 when the sequence begins, and extinguish the LED indicator light 148 when the sequence terminates.

The PROM 132 may also include instructions for the microprocessor 130 to energize the heater 136. Control of the heater 136 may range from simply being on when the air pump 58 is activated, to incorporating a delay in the triggering of the air pump 58, to preheating the aerosol solution in the solution cartridge 122 prior to initiation of air flow, to a feedback control scheme where the temperature of the solution cartridge 122 is detected and the microprocessor 130 activates the heater 136 only if the temperature is below a certain threshold.

The heater 136 can serve to heat the aerosol solution in the solution cartridge 122, thus maintaining the viscosity of the aerosol solution at a suitably low level to prevent clogging of the nebulizer unit 124. Some aerosol solutions (e.g. saccharin) may benefit from this aspect. Accordingly, automated QLFT aerosol generator 120 may be equipped to detect whether the solution cartridge 122 that is present should be heated. This may be accomplished by a toggle switch or button (not depicted) on the operator interface 144 or by having a key structure (not depicted) on the solution cartridge 122 that sets a switch when inserted in the cartridge portal 140 to either enable the power circuit to the heater 136 or to set a status switch which is checked by the microprocessor 130 before initiating the heating sequence.

It will be understood and appreciated that the methods and systems of the various embodiments may be programmed as part of one or multiple microprocessors or microcontrollers, or may be implemented as part of a PLC (Programmable Logic Controller), PAL (Programmable Array Logic), CPLD (Complex Programmable Logic Device), Digital Signal Processor (DSP), field programmable gate array (FPGA) or custom application-specific integrated circuit (ASIC), or any combination thereof, all of which are considered to be non-limiting ways in which the various embodiments of the present invention may be implemented.

Figure 7:
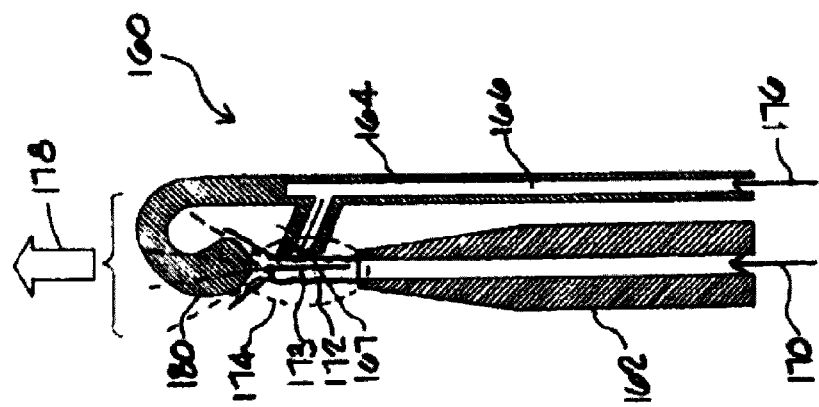
FIG. 7 is an enlarged partial view of a nebulizer structure used in the automated QLFT aerosol generator of FIG. 3.
Figure 6:
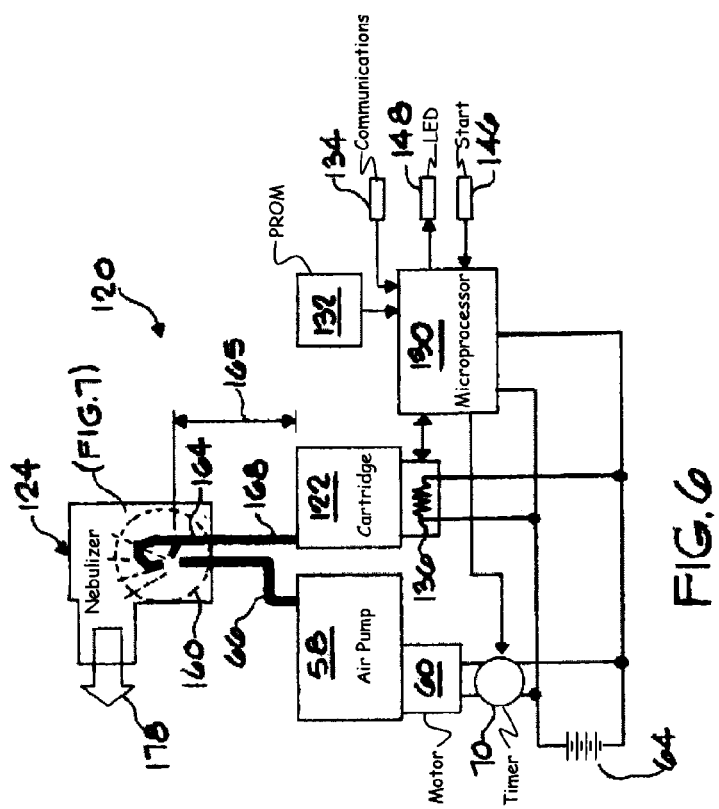
FIG. 6 is a block schematic diagram of the automated QLFT aerosol generator of FIG. 3.

A nebulizer structure 160 for operation with the solution cartridge 122 of the automated QLFT aerosol generator 120 is depicted in FIG. 7. The nebulizer structure 160 may include an aspirator nozzle 162 in fluid communication with the air pump 58 via air line 166 (FIG. 6) and a head 164 having an exit port 167 sourced by a solution source line 168 (FIG. 6) in fluid communication with the solution cartridge 122. The head and line 164, 168 are depicted as having a combined length 165 and may have a same inner diameter 166.

Functionally, the solution cartridge 122 sources the nebulizer unit 124 for generation of an aerosol. Accordingly, the nebulizer unit 124 may function without a basin. When the air pump 58 is activated, an air flow 170 is created that passes through the aspirator nozzle 162, forming an aspirator jet 172 that defines a jet axis 173 at the exit of the aspirator nozzle 162. The velocity of the aspirator jet 172 causes the static pressure of the aspirator jet 172 to be lower than the ambient pressure surrounding the nebulizer structure 160, which can create a zone of low pressure 174 proximate the jet axis 173 and in the vicinity of the exit port 167 of the head 164. The zone of low pressure 174 creates a pressure differential between the solution cartridge 122 and the exit port 167, thereby causing a flow of solution 176 that passes from the solution cartridge 122, through the solution source line 168 and head 164, out the exit port 167 and become entrained with the aspirator jet 172 to produce an aerosol 178. The nebulizer structure 160 may also include an impactor or tripping structure 180 that helps mix the aerosol 178.

The length and the inner diameter 166 of the head 164 may be sized to impart enough surface tension to the column of aerosol solution contained therein to prevent leakage of aerosol solution from the solution cartridge 122 due to gravity. Accordingly, should the unit be tipped on its side or upside down, leakage of aerosol solution from the solution cartridge 122 may thus be prevented.

At the same time, if the combined length 165 is too long, the surface tension may diminish the flow of solution 176 to an unacceptable level for the pressure differential created by the aspirator jet 172. An exemplary configuration that strikes a balance between too much and too little surface tension is a length of about 50-mm for the combined length 165 and a diameter of about 0.65-mm (about 0.025-in.) for the inner diameter 166.

The incidence of clogging of the nebulizer unit 124 may be also be reduced by increasing the effective diameter of the fluid channel over the standard dimensions found in the FT-13. Conventional nebulizers having a clearance between the aspiration nozzle and the tripping structure of about 0.038-in. and aspirator channels measuring about 0.050-× 0.023-in. have been found to operate satisfactorily with saccharin and BITREX and without clogging. Accordingly, increasing the effective distance between the aspirator nozzle tip and the tripping structure and increasing the effective diameter of the aspiration passage vis-à-vis the FT-13 may also reduce the incidence of clogging of the nebulizer unit 124.

Referring to FIGS. 8 through 10, an advanced QLFT aerosol generator 190 is depicted in an embodiment of the invention. The advanced QLFT aerosol generator may include substantially the same appurtenances and functions as the automated QLFT aerosol generator 120, as depicted in FIG. 10, plus additional aspects and function. An operator console 192 for the advanced unit in the depicted embodiment may include an array of buttons for control such as a threshold test button 194, a fit test button 196, a taste acknowledge button 198, and a pause button 200. The operator interface may also include a display 204 as depicted, such as an LCD display. Inside the console box 128, the microprocessor 130 may be operatively coupled with a data storage device such as a random access memory (RAM) 208. The RAM 208, as well as the microprocessor 130, may be accessed from via an input/output (I/O) communication device 210 such as a wireless transmitter/receiver.

In operation, the threshold test button 194 and fit test button 196 can initiate sequences that are in substantive compliance with the OSHA standard for determining, respectively, the threshold sensitivity of an individual under test (aka the "testee") and the fit integrity of the mask. The taste acknowledge button 198 may be depressed each time the testee acknowledges tasting solution, either during the threshold test or the fit test.

Actuation of the taste acknowledge button 198 may be detected by the microprocessor 130, which may record the event to the RAM 208 along with information that provides the context of the response, such as the dosage required to elicit a positive response from the testee. The I/O communication device 210 may provide access to the RAM 208 for downloading information, thereby reducing or eliminating the need for the operator to record certain information and avoiding the attendant scrivener errors.

The pause button 200 may be depressed to suspend a sequence or a series of sequences while unexpected occurrences are addressed (e.g. replacing the solution cartridge 122 or tending to collateral equipment issues). Alternatively, instead of a pause button, a "resume" button could be implemented (not depicted) wherein the sequence(s) are broken into smaller series at the end of which the algorithm is paused, only to be resumed by depressing the resume button.

The display 204 may be utilized to notify the operator which step of a given sequence the advanced QLFT aerosol generator 190 is presently executing, and/or to instruct the operator to perform a manual task before continuing on to another instruction.

Figure 11:
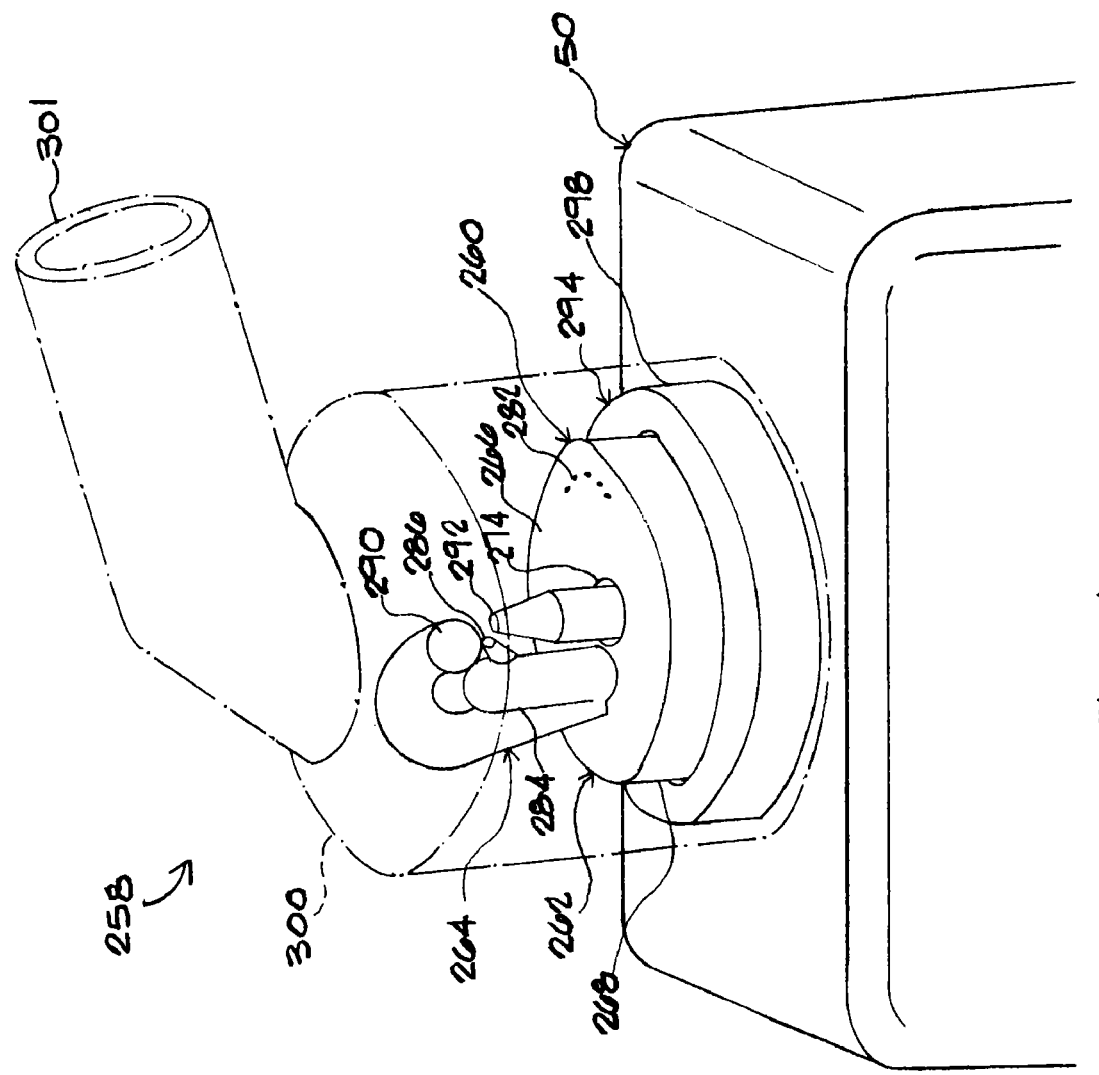
FIG. 11 is a partial perspective view of a ring cartridge and nebulizer structure operatively coupled with a hand-held, automated QLFT aerosol generator in an embodiment of the invention.
Figure 11A:
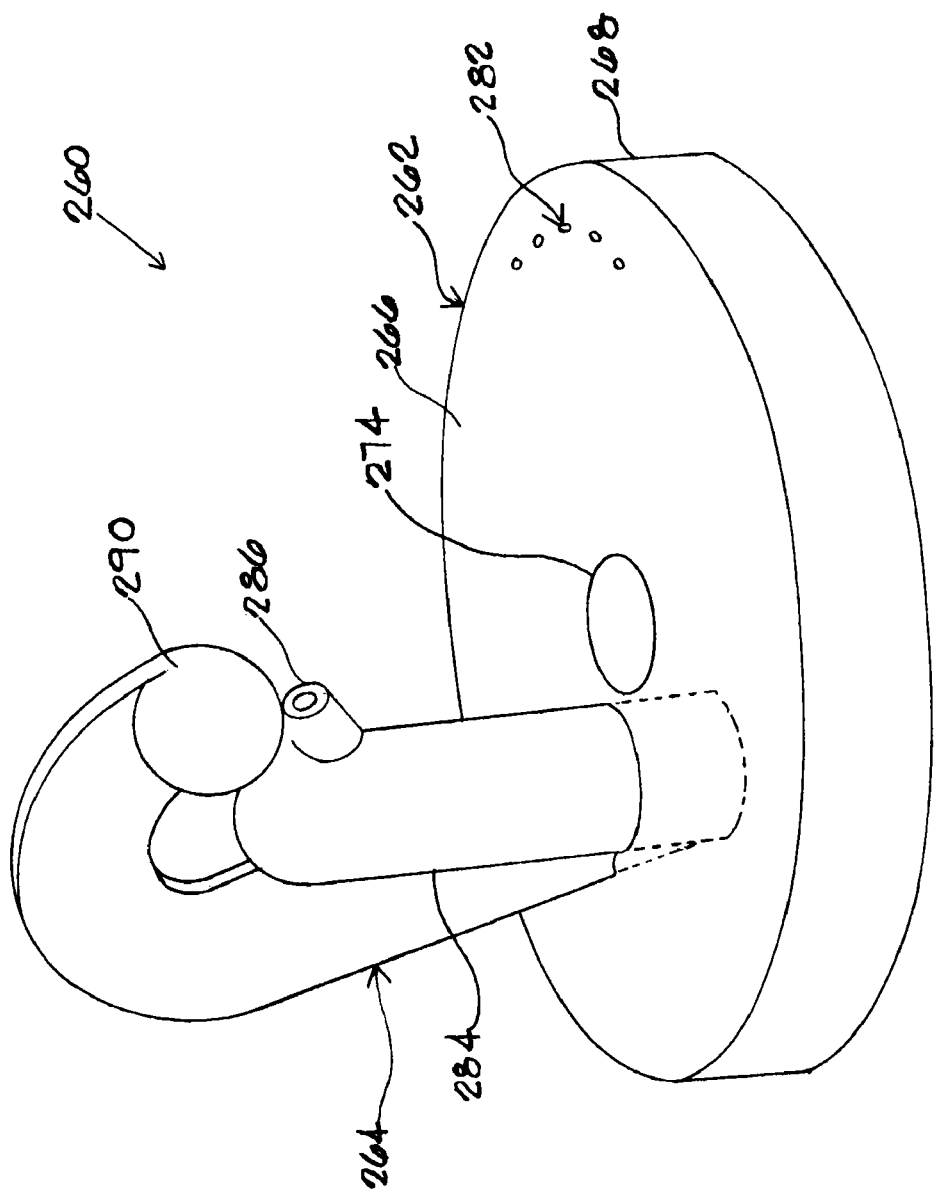
FIG. 11A is an isolated view of the ring cartridge and nebulizer structure of FIG. 11.
Figure 11B:
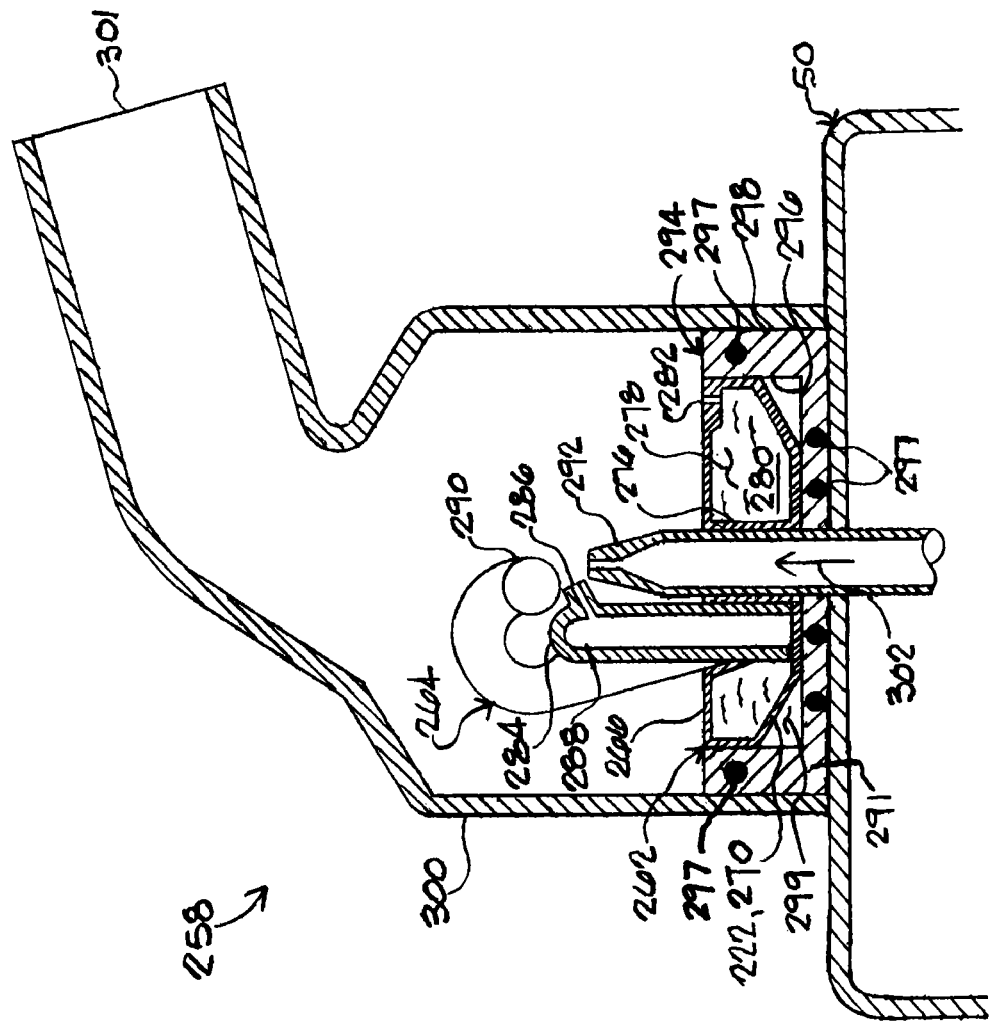
FIG. 11B is a sectional view of the ring cartridge and nebulizer structure of FIG. 11.

Referring to FIGS. 11, 11A and 11B, the automated QLFT generator 50 is depicted with a nebulizer unit 258 having an external cartridge assembly 260 in an embodiment of the invention. The external cartridge assembly 260 includes an external cartridge 262 with a nebulizer structure 264 operatively coupled thereto. In the depicted embodiment, the external cartridge 262 is substantially disk-shaped and includes an upper portion 266 that is substantially flat, side portion 268 that is substantially cylindrical, and a lower portion 270 having a sloped structure 272 akin to the surface of a frustum. A center passage 274 may pass through the external cartridge 262, the center passage 274 being defined by a tubular segment 276. The upper portion 266, side portion 268, lower portion 270 and tubular segment 276 define the boundaries of an interior chamber 278 for holding an aerosol solution 280. The external cartridge 262 may be equipped with one or more ventilation ports or apertures 282 that are in fluid communication with the interior chamber 278.

The nebulizer structure 264 may include a head 284 having an exit orifice 286 in fluid communication with the chamber 278 via a flow passage 288 within the head 284. The nebulizer structure 264 may further include a flow tripping structure 290. The nebulizer structure 264 may be integrally formed with the external cartridge 262 by a process such as injection molding. Alternatively, the nebulizer structure 264 may be formed separately and bonded to the external cartridge 262 by a process such as gluing or ultrasonic welding.

The automated QLFT generator 50 may include a nebulizer base 291 having structure for securing the external cartridge assembly 260 thereto. In one embodiment, the nebulizer base 291 may include a collar portion 294 having an inner perimeter 296 and an outer perimeter 298 and defining a receptacle 299. The nebulizer base 291 may further include heating elements 297 imbedded or operatively coupled thereto. The nebulizer base 291 may be molded integrally with the casing of the automated QLFT generator 50, or is may be fabricated separately from a metallic material.

The automated QLFT may further include an aspirator nozzle 292 extending through said nebulizer base 291 and in fluid communication with a pressure source (e.g. air pump 58 of FIG. 2). An upper housing 300 may be dimensioned to operatively couple to the collar portion 294, for example by friction fit, snap fit or a threadable engagement. The upper housing 300 may include an exhaust port 301. The external cartridge 262 may be dimensioned to couple with the inner perimeter 296 of the collar portion 294, such as by a friction fit. Alternatively or in addition, the center passage 274 may be dimensioned to snugly fit with the aspirator nozzle 292 to secure the external cartridge assembly 260 in place.

In assembly, the external cartridge assembly 260 is secured to the automated QLFT generator 50 and the upper housing 300 placed over the external cartridge assembly 260. A thermal conducting paste (not depicted) may be placed in the receptacle to fill the voids between the external cartridge assembly 260 and the receptacle 299.

In operation, an air flow stream 302 can be accelerated through the aspirator nozzle 292 to cause a zone of low pressure at the outlet of the exit orifice 286. The low pressure causes the aerosol solution 280 in the chamber 278 to be suctioned through the flow passage 288 and to be entrained in the air flow stream 302 as the air flow stream 302 exits the aspirator nozzle 292. As the flow stream 302 courses over the flow tripping structure 290, a turbulence is introduced to the flow stream 302 that may promote mixing and atomization of the entrained aerosol solution. The atomized aerosol solution propagates through the housing 300 and out the exhaust channel 301.

The heating elements 297 may be energized to provide heating to the aerosol solution 280. Using a metallic base 291 and/or utilizing a thermal conducting paste may be of benefit in transferring the heat from the heating elements 297 to the external cartridge 262. In some embodiments, heating the solution 280 may inhibit clogging of the head 284 and the exit orifice 286.

The ventilation apertures 282 enable ambient air to enter the interior chamber 278 to replace displaced aerosol solution that exits the external cartridge 262, and may be sized so that surface tension prevents the aerosol solution 280 from leaking therethrough regardless of the hydrostatic forces caused by the orientation of the external cartridge 262. If necessary, the length of the ventilation apertures 282 may be increased by increasing the thickness of the material that the ventilation apertures 282 pass through, as depicted in FIG. 11B, or by extending the passages upward above the surface of the upper portion 266 (not depicted), to enhance the surface tension effect.

The ventilation aperture or apertures 282 could also be equipped with any of several one-way flow devices (not depicted) available to the artisan that enables air to flow into the external cartridge 262 while preventing the aerosol solution 280 from flowing out. In yet another approach, the aerosol solution 280 may be actively retained by a mechanical device (not depicted) such as a valve or an adhesive strip could be operatively coupled with the ventilation aperture(s) 282 to prevent leakage when the external cartridge assembly 260 is not in use.

The ventilation aperture(s) 282 also provides a way to refill the cartridge 262. For example, a hypodermic syringe having a needle dimensioned to slidably engage one of the ventilation apertures 282 could be used as the filling device. Aerosol solution could be drawn into the syringe from a separate container, then transferred to the cartridge 262 by inserting the needle into the one of the ventilation apertures 282 and injecting the solution into the cartridge 262.

While many of the various components described and depicted above are substantially right cylindrical (e.g. external cartridge 262, tubular segment 276 and collar portion 294), other shapes may be assumed, such as elliptical, square tubular, and polygonal.

The external cartridge assembly 260 may be configured for use with standard, manually operated QLFT units such as the FT-13. For example, the nebulizer structure on the FT-13 is mounted to the aspirator nozzle (e.g. aspirator nozzle 162 of FIG. 7) and can be removed for purposes of cleaning and de-clogging. Accordingly, the external cartridge assembly 260 may be provided with instructions for an operator to remove the nebulizer structure provided with the FT-13 and install the external cartridge assembly 260 in its place. The sloped structure 272 may be configured to substantially conform to the slope of the basin 30 (FIG. 1).

An advantage provided by the external cartridge assembly 260 is to prevent spillage of aerosol solution when using the standard unit. The volume of aerosol solution available in a cartridge can also substantially exceed the volume available in the standard basin 30 by configuring the external cartridge 262 to be higher than the depth of the basin 30.

Figure 12:
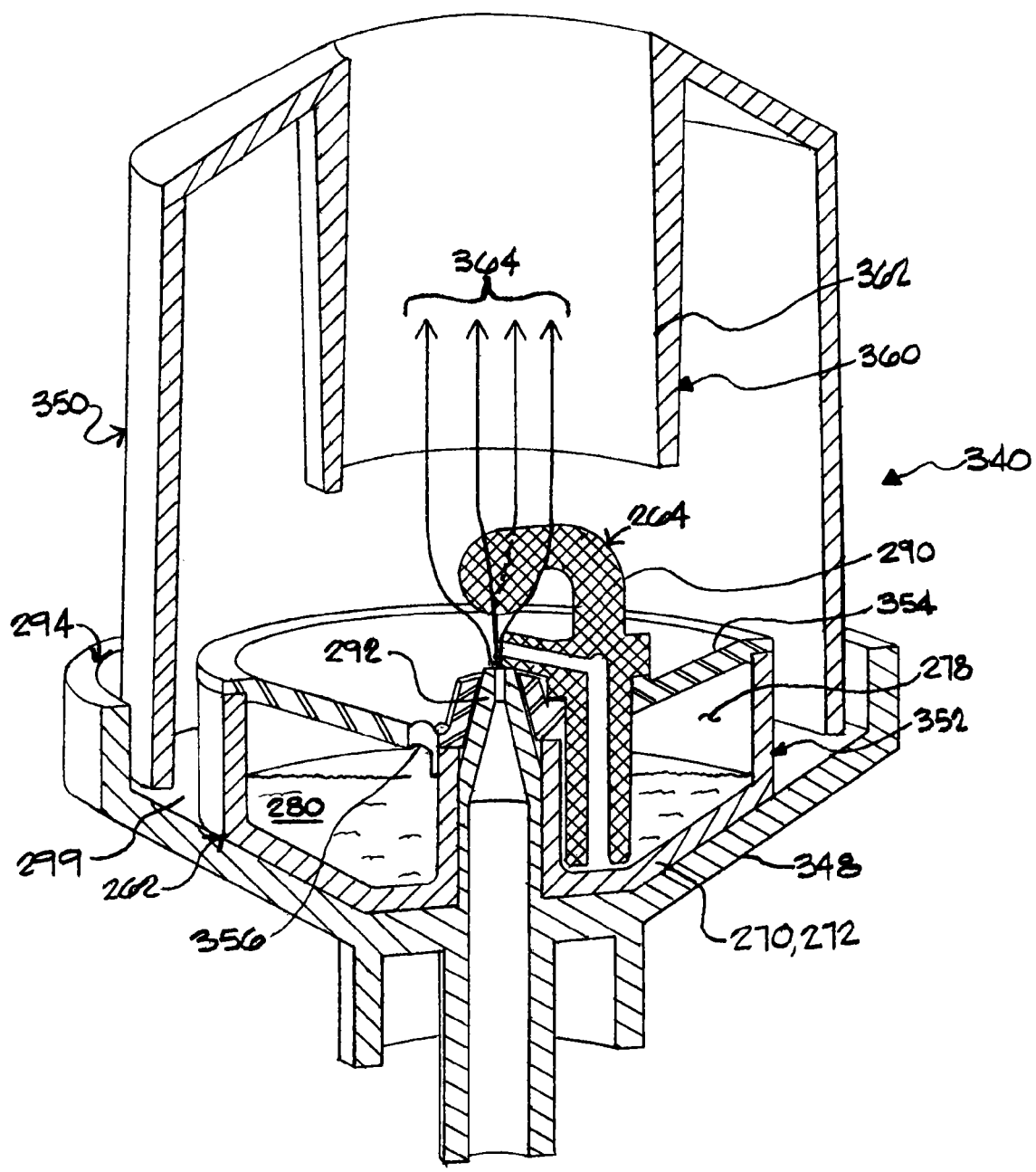
FIG. 12 is a cutaway perspective view of a nebulizer unit with a cartridge having a funnel shaped upper portion and venting port in an embodiment of the invention.

Referring to FIG. 12, a nebulizer unit 340 including a nebulizer base 348, an upper housing 350 and a cartridge assembly 352 is depicted in an embodiment of the invention. In the depicted embodiment, the cartridge assembly 352 includes a funnel shaped upper portion 354 with a centrally located venting port 356 and a collector 360. While only the single centrally located venting port 356 is depicted, it is understood that a plurality of centrally located venting ports may also be utilized. The collector 360 may extend from a lower portion of the exhaust channel 301 (FIGS. 11 and 11B). The nebulizer unit 340 may otherwise include many of the same aspects as the nebulizer unit 258, which are given the same numerical references as in FIGS. 11, 11A and 11B.

In operation, aerosol solution is drawn from the cartridge, entrained in the aspirator jet and atomized in the form of vapor or aerosol droplets as described in connection with FIG. 11B. A portion of the atomized solution comprising vapors and smaller droplets of aerosol solution flows upward from the tripping structure 290, following flow streamlines 364 of the gas flow through the collector 360 and out of the upper housing 350. At least part of the remaining portion of the atomized solution comprising larger aerosol droplets may tend to follow a trajectory substantially independent of the flow streamlines 364 and impinge on an interior surface 362 of the collector 360. Aerosol solution that thereby accumulates on the an inner perimeter 362 of the collector 360 may gather in the form of drops that, by the influence of gravity, run down the inner perimeter 362 to drip onto the funnel shaped upper portion 354. The funnel shaped upper portion 354 serves as a catch basin that directs the accumulation of aerosol solution 280 from the drops to the centrally located venting port 356 for reentry into the cartridge assembly 352. In this way, the venting port 356 not only vents cartridge assembly 352 but also serves to return aerosol solution 280 to the cartridge assembly 352 for reuse.

Recall the discussion attendant FIG. 11B whereby venting ports can be dimensioned so that tension forces prevent the aerosol solution from escaping the cartridge by hydrostatic forces. It is noted that the venting port 356 can be designed this way without adversely affecting the ability of the aerosol solution to be returned to the interior chamber 278 of the cartridge. This is because a suction is created within the interior chamber 278 during operation by the displacement of the aerosol solution that exits the cartridge. Accordingly, the suction can overcome the tension forces that would otherwise prevent the aerosol solution from entering the interior chamber via hydrostatic forces and draw the aerosol solution back into the cartridge for reuse.

Referring to FIGS. 13 through 16, an automated QLFT generator 370 including a hand-held console box 372 is depicted in an embodiment of the invention. The automated QLFT generator 370 includes a receptacle portion 374 and a nebulizer base 376 having a window 382 and that secures a nebulizer unit 380. The motor, pump, power source (not depicted) and nebulizer base 376 for the automated QLFT generator 370 embodiment were taken from a Mobineb portable compressor nebulizer, manufactured by Apex Medical Corp., Taipei County, Taiwan, with the nebulizer unit 380 modified to include certain aspects described below.

The nebulizer unit 380 may include a cartridge assembly 386 and a removable housing 388, the removable housing 388 including a flow impactor 390. The nebulizer base 376 may include an air supply port 462 that engages the nozzle portion 396 of the cartridge assembly 386 to secure the cartridge assembly 396 in place.

The cartridge assembly 386 may include a cylindrical lower portion 394, a nozzle portion 396 and an upper portion 398, all of which cooperate to define an inner chamber 402 for containing an aerosol solution 404. In one embodiment, the nozzle portion 396 includes an inlet portion 406 and a converging portion 408. A sight glass 409 may be included on the cylindrical lower portion 394 for viewing the contents of the inner chamber 402. The cartridge assembly 386 may also include a lip portion 410 that extends upward from the cylindrical lower portion 394 of the cartridge assembly 386.

The upper portion 398 of the cartridge assembly 386 may comprise a flange portion 414 and a standoff cylinder 416. A nozzle shroud 418 may depend from the standoff cylinder 416. The standoff cylinder 416 and nozzle shroud 418 may cooperate to define a catch basin 420. The catch basin 420 may include structure that defines one or more venting ports 422 that provide fluid communication between the inner chamber 402 and the atmosphere external the cartridge assembly 386.

One or more bypass channels 426 may be formed on the interior surface of the nozzle shroud 418. The nozzle shroud 418 and the nozzle portion 396 may be dimensioned to form a tight fit upon assembly of the cartridge assembly 386, such that the bypass channels 426 are essentially liquid tight.

Figure 14:
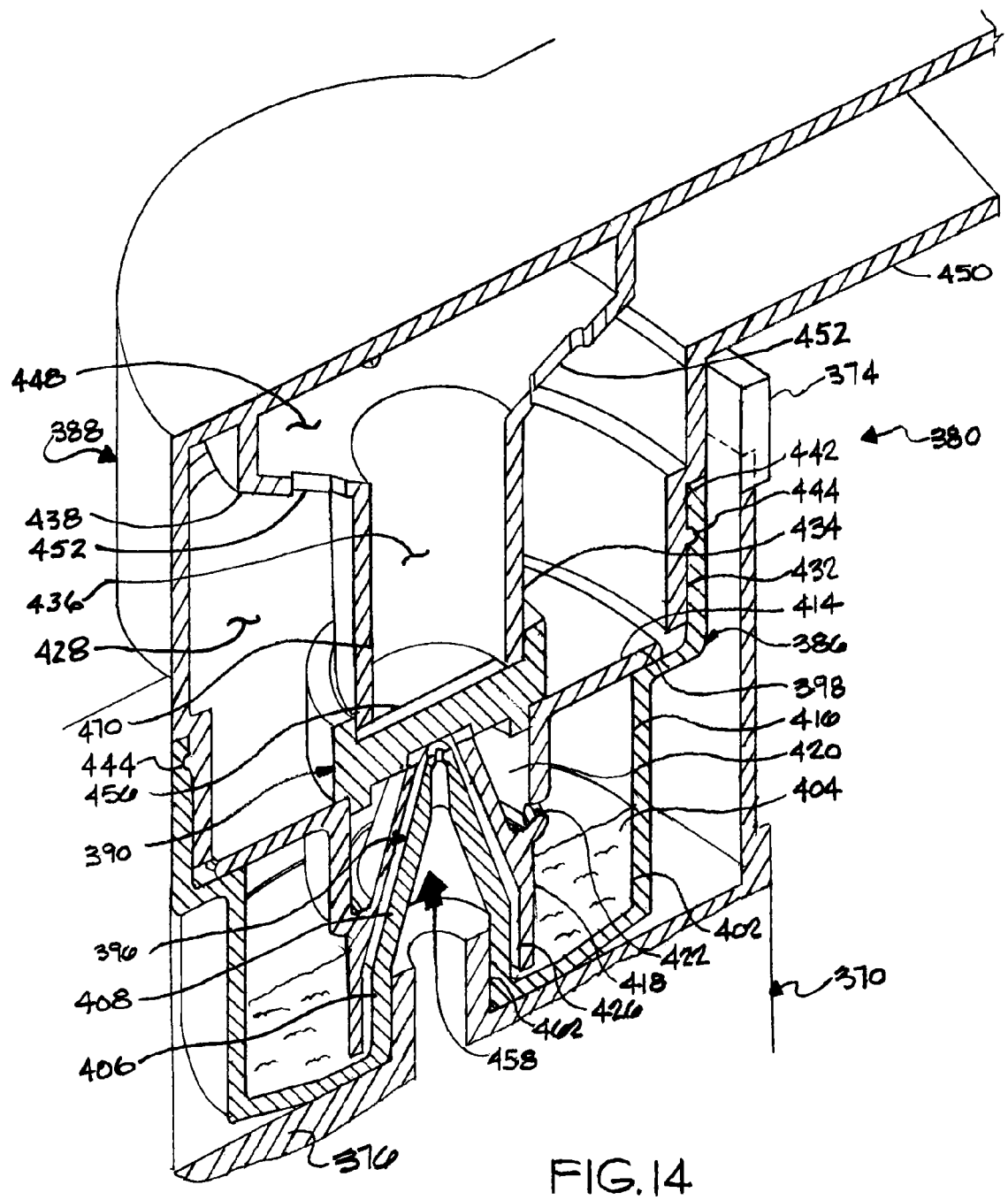
FIG. 14 is a cutaway perspective view of a nebulizer unit of FIG. 13 comprising a replaceable cartridge assembly in an embodiment of the invention.
Figure 15:
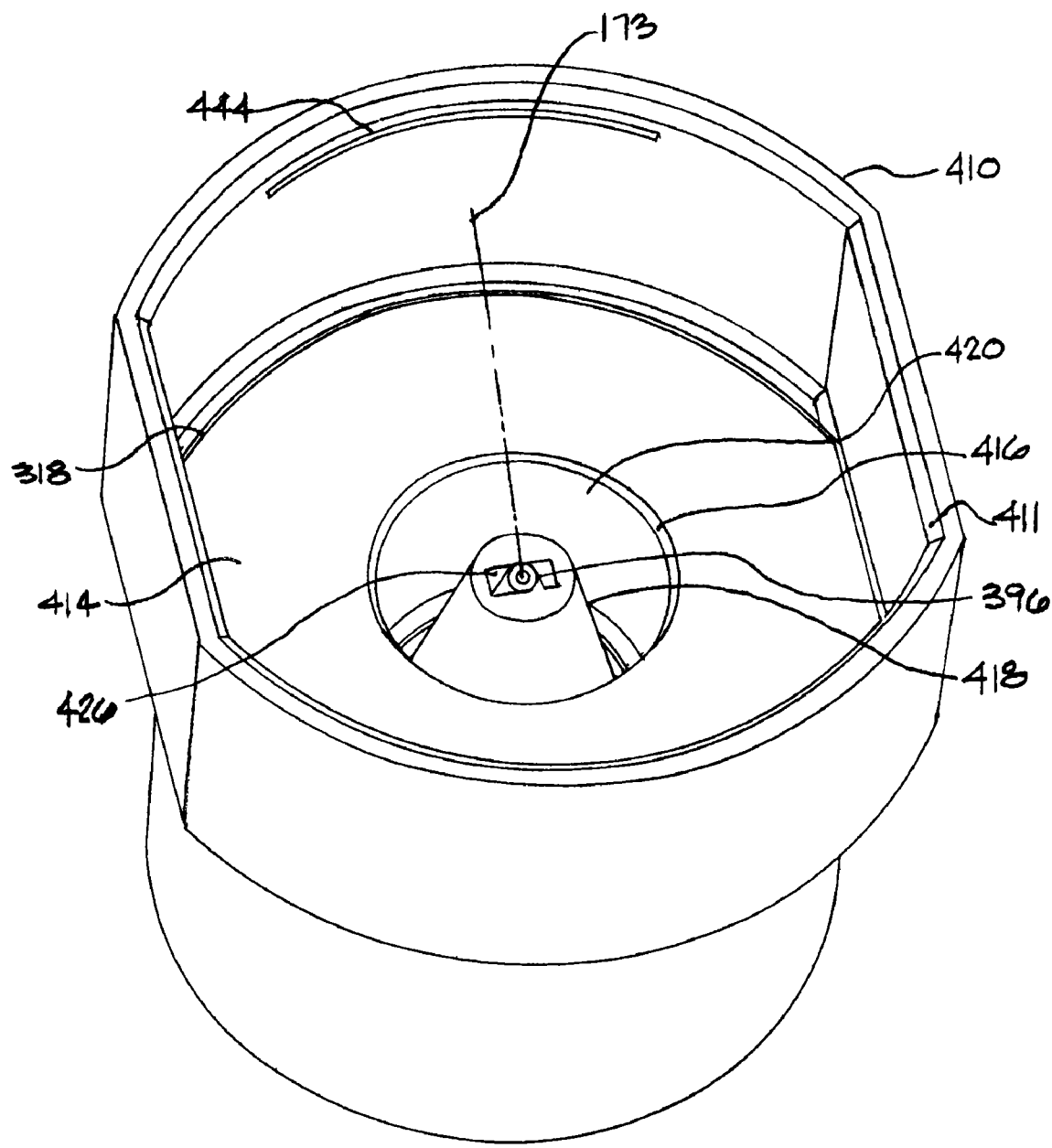
FIG. 15 is a perspective view of the replaceable cartridge assembly depicted in FIG. 14.
Figure 16:
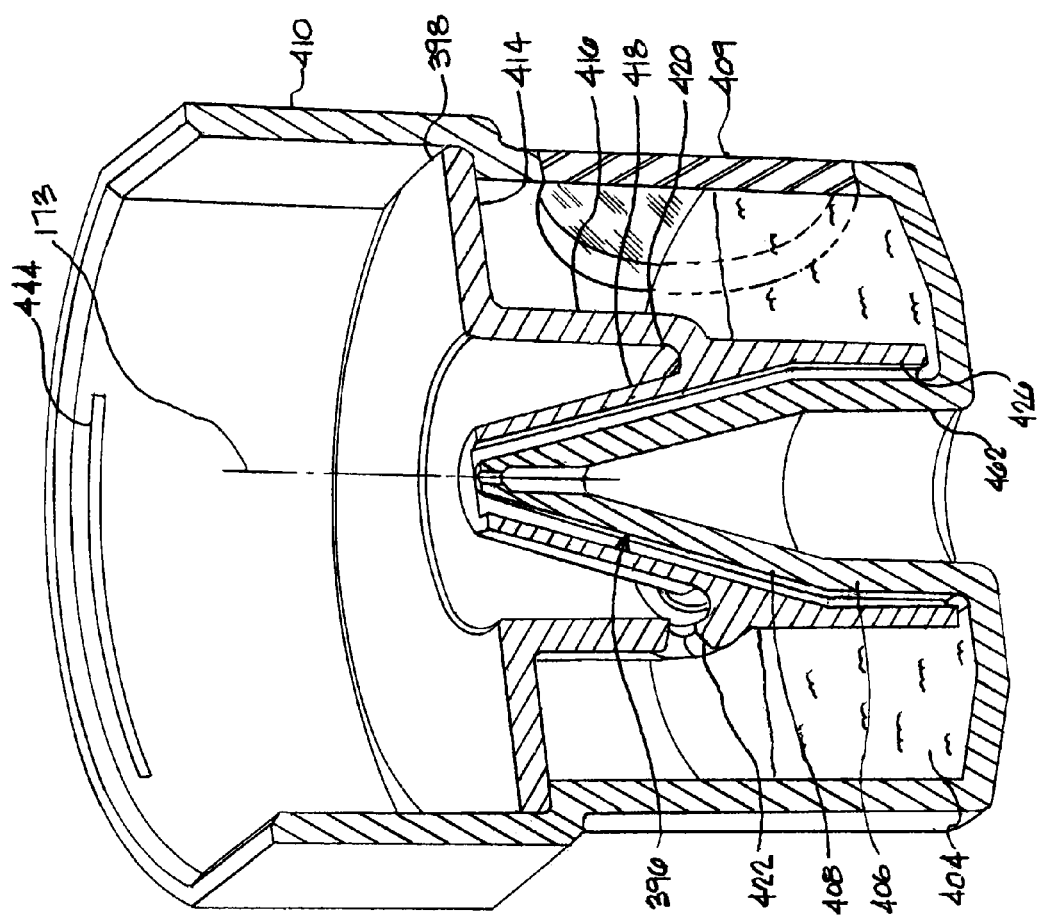
FIG. 16 is a cutaway perspective view of the replaceable cartridge assembly depicted in FIG. 14.

The removable housing 388 may cooperate with the cartridge assembly 386 to define a flow chamber 428. In one embodiment, the removable housing 388 includes an outer cylinder 430 having a lip portion 432 and an interior cylinder 434 that defines a flow channel 436 connected by a web portion 438. The lip portion 432 of the outer cylinder 430 may be dimensioned to mate with the lip portion 410 of the cartridge assembly 386. The lip portions 432 and 410 may be equipped with detents 442 and grooves 444 that interlock (FIG. 14). The removable housing 388 and the cartridge assembly 386 may also be held in place by a friction fit between the lip portions 432 and 410.

The web portion 438 may define an upper chamber 448. The upper chamber 448 is in fluid communication with an exhaust port 450 via a plurality of through-slots 452 that are formed in the web portion 438.

The flow impactor 390 may be operatively coupled with the base of the interior cylinder 434 and proximate the upper portion 398 within the nebulizer unit 380. The flow impactor 390 may further include a tripping structure 456 that is aligned over the nozzle portion 396 of the cartridge assembly 386 so as to intersect or obstruct an air flow stream 458 that may flow through the nozzle portion 396.

In operation, the air flow stream 458 may be introduced through the air supply port 462, flowing through the nozzle portion 396 and impinging on the tripping structure 456 of the flow impactor 390. The air flow stream 458 and flow impactor 390 may cooperate to create a low pressure zone proximate the tip of the nozzle portion 396 and nozzle shroud 418 at the exit of the bypass channels 426. The low pressure zone draws the aerosol solution 404 from the inner chamber 402 via the bypass channels 426 of the nozzle shroud 418 and entrains the aerosol solution 404 within the air flow stream 458. Substantial liquid tightness of the bypass channels 426, though not required, provides the advantage of efficiency in the drawing of the aerosol solution 404 therethrough. It is further noted that arranging the bypass channels 426 in the same plane as the tripping structure 456, as depicted in FIG. 14, generally enhances the creation of the low pressure zone.

The tripping structure 456, though of a different geometry, performs the same function as the tripping structure 290 of FIG. 12. Moreover, the interior cylinder 434 serves as a collector for aerosol droplets that impinge thereon. The aerosol solution that collects on the interior cylinder/collector 434 and the web portion 438 forms drops that, by gravity, run down the interior surface 470, into the catch basin 420 and into the inner chamber 402 via the venting ports 422 for reuse.

Figure 13:
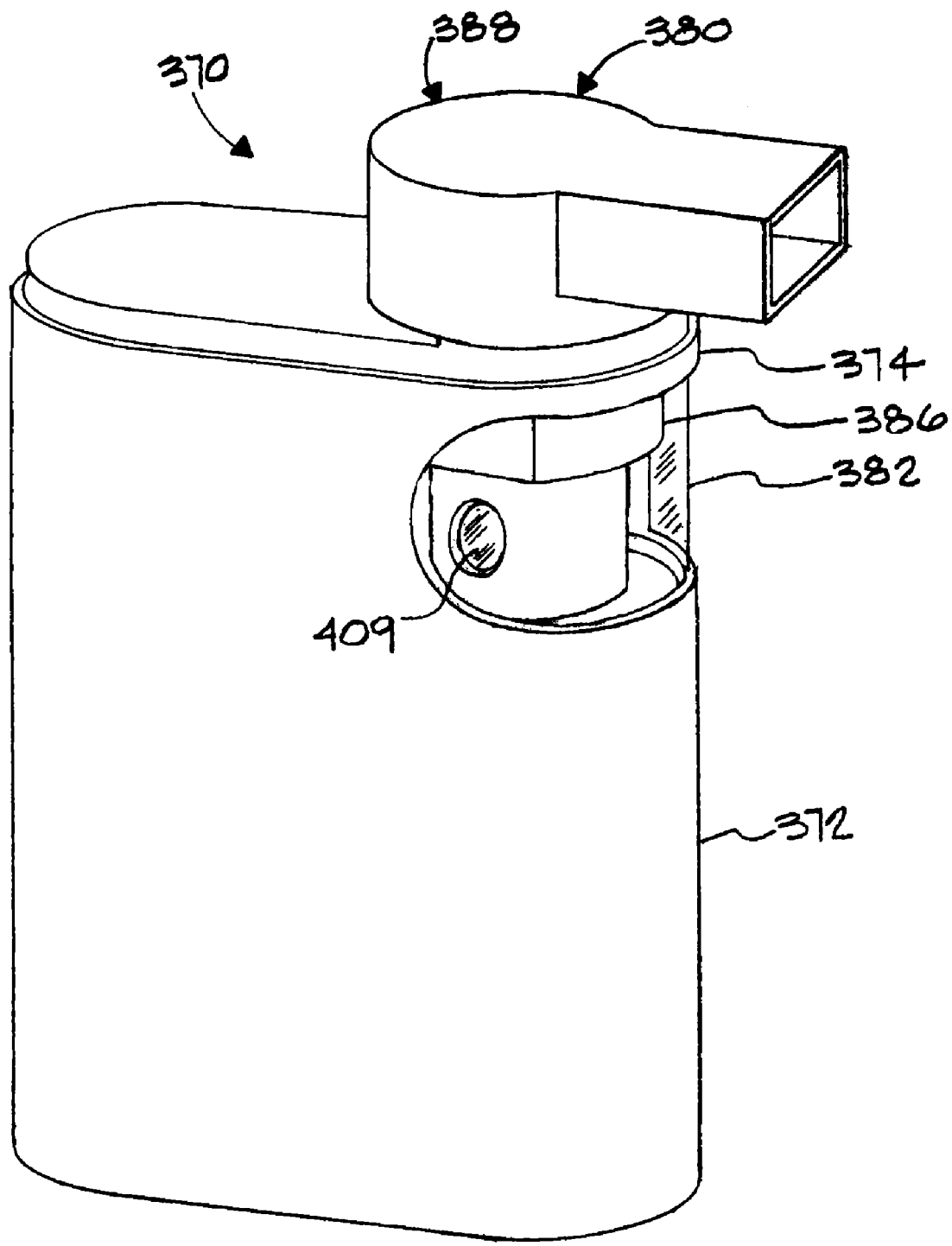
FIG. 13 is a perspective view of an automated QLFT generator in an embodiment of the invention.

The automated QLFT generator 370 may be an advanced unit with various aspects described in connection with the advanced QLFT aerosol generator 190, such as the a microprocessor, memory devices and operator interface (not depicted in FIG. 13).

To install the cartridge assembly 386, the air supply port 462 of the automated QLFT generator 370 is inserted into the inlet portion 406 of the nozzle portion 396 with the removable housing 388 removed. The removable housing 388 is then mated with the cartridge assembly 386 to form the flow chamber 428. The lip portion 432 of the removable housing 388 and the cartridge lip 410 may be snap locked into place using the detents 442 and grooves 444.

Removal of the cartridge assembly 386 is accomplished by exerting a force on the nebulizer unit 380 that pulls away from the automated QLFT generator 370. By this action, either the removable housing 388 is decoupled and lifted away from the cartridge assembly 386, or the nebulizer unit 380 is decoupled from the air supply port 462 of the automated QLFT generator 370. In the former case, the cartridge assembly 386 is then unsnapped from the removable housing 388 to free the cartridge assembly 386. In the latter case, the cartridge assembly 386 is then decoupled from the air supply port 462 of the automated QLFT generator 370 and removed from the receptacle 464.

The window 382 may be used when installing the cartridge assembly 386 or nebulizer unit 380 within the receptacle portion 374 to aid the operator in aligning the nozzle portion 396 with the air supply port 462. The window 382 may also enable the operator to view the sight glass 409 to check the level of aerosol solution 404 remaining in the inner chamber 402 of the cartridge assembly 386. The sight glass 409 may include graduations enabling the operator to determine the relative amount of aerosol solution 404 remaining in the cartridge assembly 386.

Figure 17:
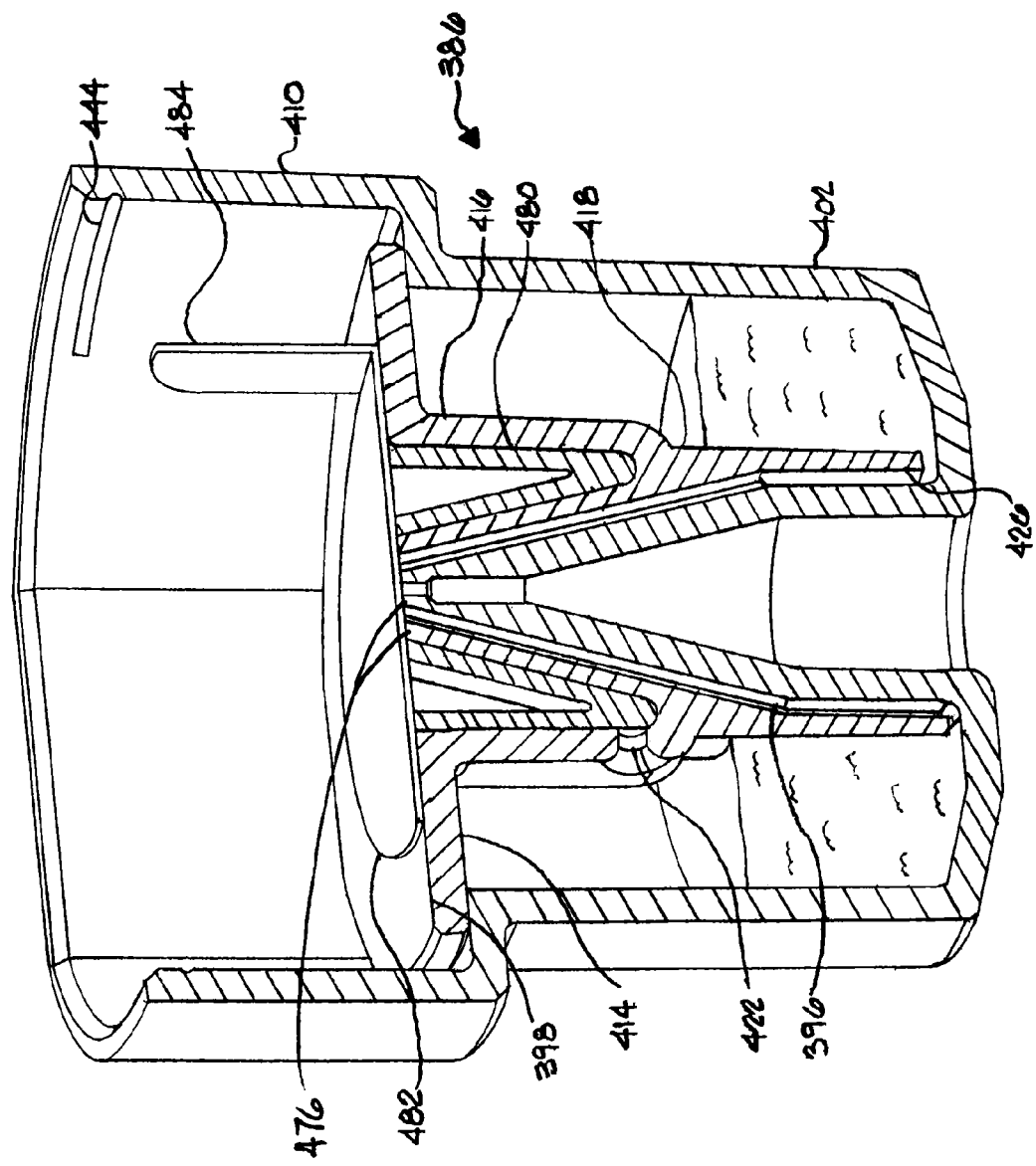
FIG. 17 is a cutaway perspective view of the replaceable cartridge assembly depicted in FIG. 14 further comprising a cap secured by an adhesive strip for sealing the cartridge assembly during shipping and handling.

Referring to FIG. 17, the cartridge assembly 386 is presented in a configuration that is amenable to shipping. A plug 480 may be disposed within the catch basin 420 to seal the venting ports 422. An adhesive strip 482 may be placed in sealing contact over the flange portion 414 and tip portions 476 of the nozzle portion 396 and nozzle shroud 418. The adhesive strip 482 may also be affixed to the plug 480. A tab portion 484 may extend from the adhesive strip 482.

Functionally, the plug 480 may provide a liquid tight seal of venting ports 422 and may be held within the catch basin 420 by a friction fit. The adhesive strip 482 may serve to further secure the plug 480 in place. The adhesive strip 482 may also prevent the aerosol solution 404 from escaping the inner chamber 402 through the bypass channels 426 by providing a sealed barrier at the tip portions 476 of the nozzle portion 396 and the nozzle shroud 418 that prevents the aerosol solution 404 from escaping to the catch basin 420 or plug 480, as well as to the exit of the nozzle portion 396.

In operation, the user pulls on the tab portion 484 to remove the adhesive strip 482 to lift it away from the sealing engagement with the flange portion 414 and the tip portions 476. The bond between the adhesive strip 482 and the plug 480 may be enhanced so at the plug 480 stays with the adhesive strip 482 upon removal of the adhesive strip 482. Alternatively, the plug 480 may be removed after removal of the adhesive strip 482. Removal of the adhesive strip 482 and the plug 480 unseals the bypass channels 426 and the venting ports 422, respectively, and makes the cartridge assembly ready for use.

Figure 18:
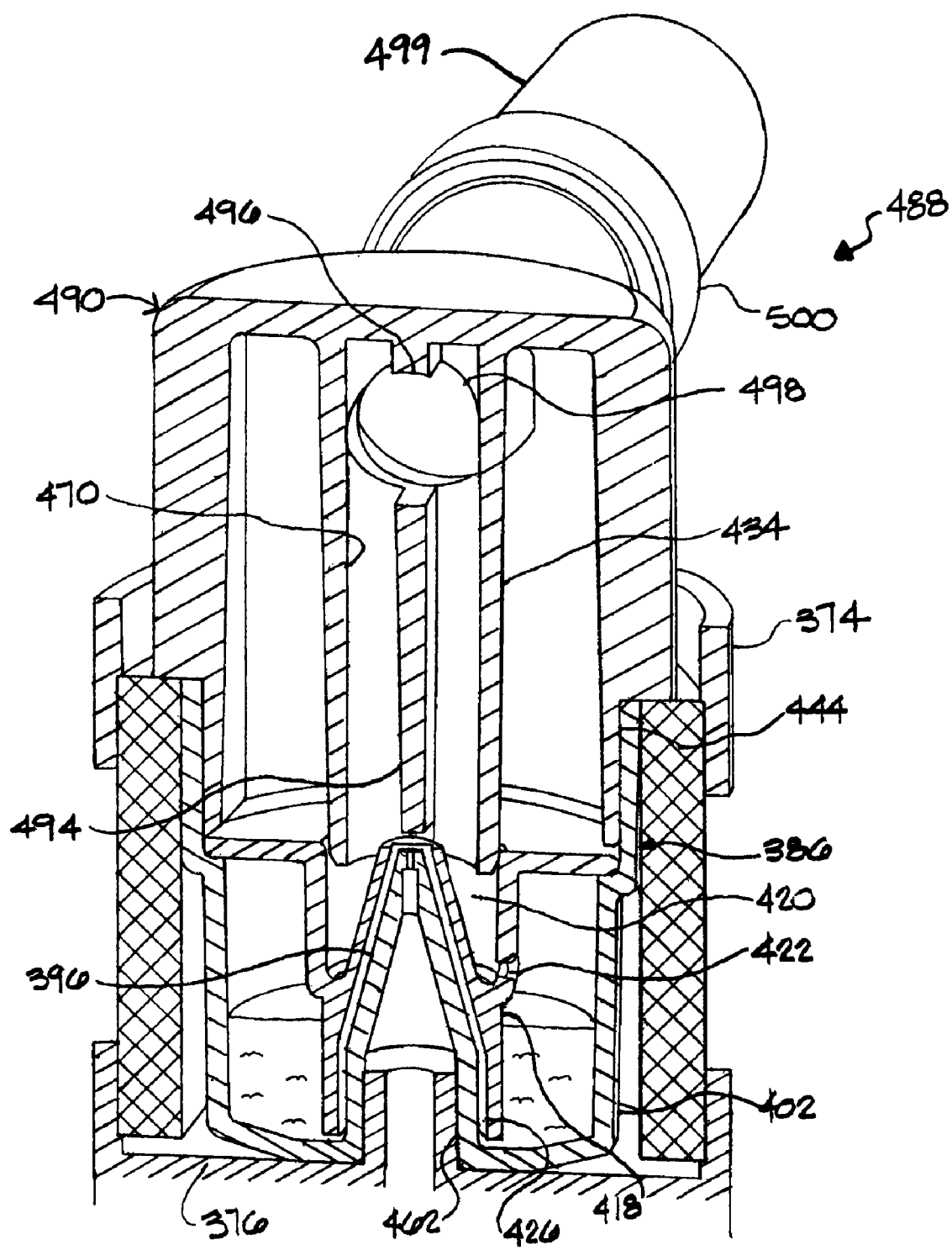
FIG. 18 is a nebulizer unit having an axial rib tripping structure in an embodiment of the invention.

Referring to FIG. 18, a nebulizer unit 488 having an alternative removable housing 490 is depicted in a variation of the invention. Many of the aspects of the depicted embodiment are the same as with the nebulizer unit 380, and are identified with like numbered numerical references. In the depicted embodiment, the removable housing 490 includes a rib 494 extending the length of the interior cylinder 434. A rib vent 496 and a channel vent 498 enable the atomized aerosol solution to exit the interior cylinder 434. The removable housing 490 may comprise an exhaust port 499 having an extended length. The exhaust port 499 may further comprise a separable joint 500.

Functionally, the lower extremity of the rib 494 serves as the flow impactor/tripping structure. The collector/interior cylinder 434 can capture atomized solution that is sprayed off the lower extremity of the rib 494 for collection and transfer to the catch basin 420. An advantage of the nebulizer unit 488 is that the rib 494 is readily molded integrally with the collector/interior cylinder 434, thus negating the need to mold a tripping structure and assemble it onto another component as a separate part, such as required with the nebulizer unit 380. The extended length of the exhaust port 499 allows for greater separation between the operator of the nebulizer unit 380 and the testee. To facilitate easy storage of the nebulizer unit 380, the separable joint 500 allows for the exhaust port 499 to be separated for easy storage of the nebulizer unit.

Figure 19:
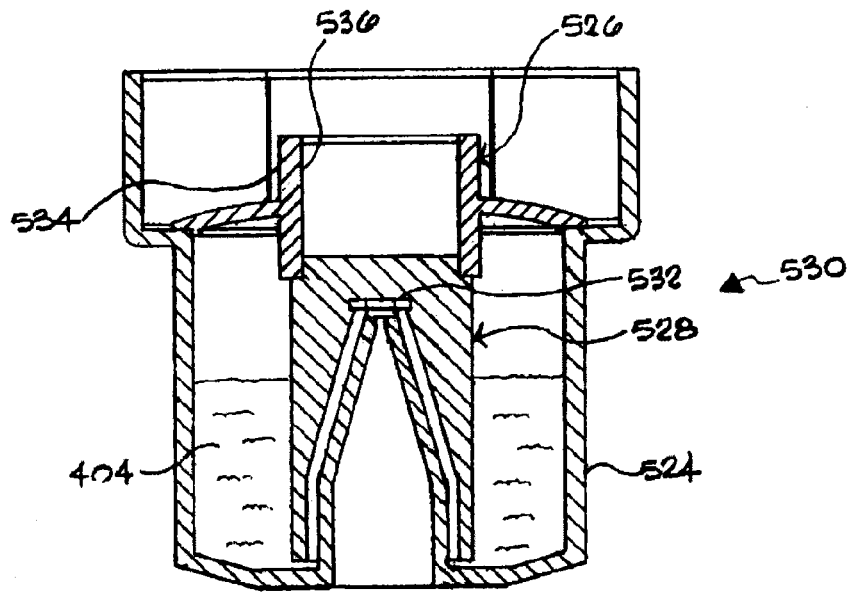
FIG. 19 is a cutaway side view of the cartridge assembly having a flow impactor in an embodiment of the invention.

Referring to FIG. 19, a cartridge assembly 530 including a cylindrical lower portion 524, a cap portion 526, a flow impactor 528 and a collector 534. Functionally, the cap portion 526 not only helps retain the aerosol solution 404 within the cartridge, but can also hold the flow impactor 528 in place within the assembly. In operation, because the cartridge assembly 530 provides its own flow impactor 528, the cartridge assembly 530 may be used with housings that do not include a flow impactor. The collector 534 captures aerosol solution 404 that collects on an interior wall 536 of the collector 534 for return to the cartridge assembly 530.

Referring to FIGS. 20A and 20B, a nebulizer unit 560 is depicted in an embodiment of the invention. As in other embodiments, the nebulizer unit 560 may include a cartridge assembly 564 and a removable housing 566. The cartridge assembly 564 may include a cylindrical lower portion 565 that cooperates with an upper portion 567, the upper portion 567 defining a catch basin 568 with a venting port 570. The removable housing 566 may include an outer cylinder 572 concentric with a collector 574. A flow impactor 576 may be attached to the collector 574.

A distinction of the nebulizer unit 560 is the presence of a bifurcated nozzle 580. The bifurcated nozzle 580 in the depicted embodiment comprises a lower nozzle portion 582 and an upper nozzle portion 584. In one embodiment, the lower nozzle portion 582 is part of the cartridge assembly 564 and the upper nozzle portion 584 is joined to or integral with the flow impactor 576. (For purposes of this disclosure, a component is "integral" with another component if the components were formed as the same part. Therefore, components that are integral are in contrast to components that are joined.)

At least one bypass channel 586a may be defined in the lower nozzle portion 582 between the upper portion 567 and cylindrical lower portion 565 of the cartridge assembly 564. The upper nozzle portion 584 may also include a bypass channel 586b. The upper portion 567 may further include a ring-shaped barrier 588 that surrounds the catch basin 568. A pull tab seal 590 may be placed over the top of the lower nozzle portion 582 and the catch basin 568 of the cartridge assembly 564.

In assembly, the pull tab seal 590 is removed from cartridge assembly 564 (FIG. 20A) and the removable housing 566 coupled to the cartridge assembly 564 (FIG. 20B). Bypass channels 586a and 586b may be aligned by virtue of a keyed shape, such as a non-circular shape at the interface of the removable housing 566 and the cartridge assembly 564. (See, e.g., the flat portion 411 of the cartridge lip 410 of the cartridge assembly in FIG. 15. Such a flat 411, cooperating with a complimentary flat on a removable housing 566, would orient the upper and lower nozzle portions 584, 582 so that the bypass channels 586a and 586b are in alignment.) In operation, the aerosol solution 404 is aspirated through the bypass channels 586a and 586b, akin to the nebulizer assemblies 380 and 488.

An advantage of the nebulizer unit 560 is that the venting port 570 may be located at a higher elevation, enabling more aerosol solution 404 to be stored within the cartridge assembly. The catch basin 568 per se will have has less capacity. However, the ring-shaped barrier 588, where utilized, combines with the catch basin 568 to effectively increase the capacity.

A primary difference between the manual QLFT aerosol generator 20 and the various automated aerosol generators disclosed herein is the manner of delivery. The manual QLFT aerosol generator 20 requires actuating the squeeze ball pressure generator 22 to deliver the aerosol. At question is how to bring the automated QLFT devices disclosed herein into substantive compliance with OSHA protocols. By "substantive compliance," it is understood because the OSHA standard is written in terms of actuation (squeezing) of the squeeze ball pressure generator 22 of the manual QLFT aerosol generator 20, the automated QLFT aerosol generators of the instant invention, which are not actuated in this manner, cannot execute the OSHA standard in literal terms. Rather, as discussed below, the various automated QLFT generators (e.g., QLFT generators 190 and 370) can be operated in a way that delivers substantially the same mass of solution or mass of non-volatiles suspended in solution as the manual QLFT aerosol generator 20.

The OSHA protocol for sensitivity and fit testing with the manual QLFT aerosol generator 20 calls for actuating the squeeze ball pressure generator 22 in sets of five or in sets of 10 actuations. Accordingly, a test was developed to determine the mass of the non-volatile agent suspended in solution for 10 actuations of the squeeze ball pressure generator 22 of the manual QLFT aerosol generator 20. Effectively, the manual QLFT aerosol generator 20 serves as a secondary standard to the OSHA protocol by this approach.

Figure 21:
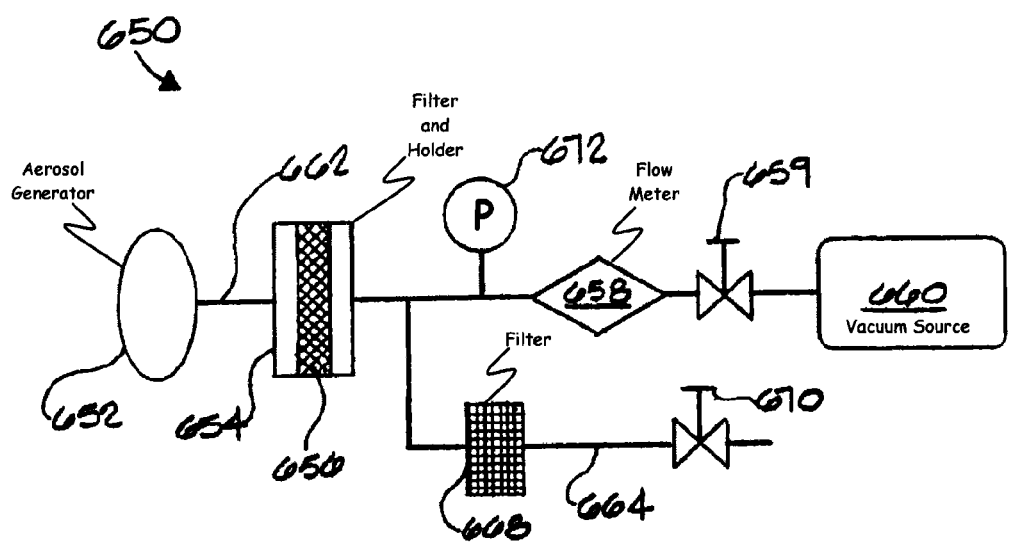
FIG. 21 is a schematic of a mass dose test setup in an embodiment of the invention.

Referring to FIG. 21, a test setup 650 for determining a mass dose of a QLFT aerosol generator is depicted in an embodiment of the invention. Herein, a "mass dose" is the amount of mass (either solution mass or suspended non-volatiles mass) produced by a known aerosol-producing metric, such as number of squeeze ball actuations or operating time of a pump. Also, a "normalized mass dose" is a mass dose per unit of aerosol-producing metric, e.g., mg/squeeze or mg/second.

The test setup 650 may include a QLFT aerosol generator 652 (e.g., the manual QLFT aerosol generator 20 or an automated device such as one of the automated QLFT generators 50 or 370), a filter holder 654 for holding a filter 656, a flow meter 658, a metering valve 659 and a vacuum source 660, all in fluid communication with each other via a testing line 662. A bypass line 664 may be disposed between the filter holder 654 and the flow meter 658. A filtering device 668 such as a HEPA filter may be placed in the bypass line 664. In addition to or as an alternative to the flow meter 658, a variable restriction device 670 may be included in the bypass line 664, and a pressure gauge 672 operatively coupled with the testing line 662.

In operation, the QLFT aerosol generator 652 is operatively coupled with the filter holder 654 and air drawn through the bypass line 664 and the testing line 662 downstream of the filter holder 654 by opening the metering valve 659 to expose the circuit to the vacuum source 660. The variable restriction device, when present, may also be adjusted to vary the level of vacuum in the testing line 662.

When the aerosol generator 652 is activated, aerosol emanating therefrom may be drawn into the filter holder 654 by the vacuum present downstream of the filter holder 654. The filter 656 may be selected so that substantially all of the aerosol solution droplets suspended in the aerosol are captured by the filter 656. Prior to insertion into the filter holder 654, the filter 656 may be weighed. After exposing the filter to the aerosol generated by the aerosol generator 652, the filter 656 may be dried and weighed again. The difference between the pre- and post-exposure filter weighings may be presumed to be the mass of agent captured by the filter 656 that serves as the basis of the mass dose determination. It is noted that alternative approaches to determine mass doses could also be utilized. For example, the filter 656 would not have to be dried, but could be weighed wet to determine the mass dose. Also, solution could be captured and the mass determined other ways, such as Tapered Element Oscillating Microbaolance (TEOM).

Example mass doses of the manual QLFT aerosol generator 20 and the automated QLFT generator 370 were determined in accordance with Tests 1 and 2, respectively, described below. Each test was performed to characterize the respective QLFT aerosol generators for four aerosol solutions: (1) BITREX fit solution, (2) saccharin fit solution, (3) BITREX sensitivity solution and (4) saccharin sensitivity solution. The results of Tests 1 and 2 are presented in Table 1 below.

Test 1

The manual QLFT aerosol generator 20 was operatively coupled to the test setup 650 and the squeeze ball pressure generator 22 actuated enough times in succession to produce enough of a mass dose to be detected on the filter 656 after drying. The number of actuations required depended on the aerosol solution under test because of the nature of the agents in suspension and the differing concentration levels between the fit and sensitivity test solutions. The resultant captured mass was normalized against the number of actuations of the squeeze ball pressure generator 22 that produced the captured mass to provide the normalized mass dose in units of mg/squeeze.

Test 1 was repeated 5 times to establish a statistical mean $\mu$ and statistical standard deviation $\sigma$ of the normalized mass doses of the specific QLFT aerosol generator 652 and aerosol solution under test. The variability of the averages was expressed by a "coefficient of variation," given by $$\frac{\sigma}{\mu} \cdot 100\% \quad \text{Eqn. (1)}$$

Test 2

The automated QLFT generator 370 was operated for a period of time sufficient to produce enough of a mass dose to be detected on the filter 656 after drying. The time period required depended on the aerosol solution under test because of the nature of the agents in suspension and the differing concentration levels between the fit and sensitivity test solutions. The resultant captured mass was normalized against the run time of the pump that produced the captured mass to provide the normalized mass dose in units of mg/second. The coefficient of variation for Test 2 was determined using Eqn. (1).

The amount of run time of the automated QLFT generator 370 to produce the same amount of mass for one actuation of the squeeze ball pressure generator 22 is obtained by dividing the normalized mass dose of the manual QLFT aerosol generator 20 by the normalized mass dose of the automated QLFT generator 370, the quotient having effective units of seconds/squeeze. An equivalent of run time of the automated QLFT generator 370 to produce an equivalent mass dose of the manual QLFT aerosol generator 20 may then be obtained by multiplying that quotient by the number of squeezes for a mass dose of the manual QLFT aerosol generator 20. The results of the equivalent run time to produce the mass dose of 10 squeezes of the squeeze ball pressure generator 22 are presented in Table 1 for the different aerosol solutions.

The differing results of the various normalized mass doses and the equivalent run times for the respective aerosol solutions may be the result of differing fluid properties (e.g. concentration, density and viscosity). It is further noted that the variability of the delivered dose was lower for all of the automated QLFT generator tests than for the manual FT-13 standard, as evidenced by the lower coefficient of variation.

TABLE 1

| Aerosol Solution | Normalized Mass Dose | | Equivalent | Coefficient of Variation | |
|---|---|---|---|---|---|
| | Manual QLFT (mg/squeeze) | Automated QLFT (mg/second) | Run Time (seconds per 10 squeezes) | Manual QLFT | Automated QLFT |
| BITREX Fit | 0.015 | 0.031 | 5.0 | 50% | 17% |
| Saccharin Fit | 0.079 | 0.248 | 3.2 | 50% | 16% |
| BITREX Sensitivity | 0.018 | 0.024 | 7.5 | 22% | 21% |
| Saccharin Sensitivity | 0.004 | 0.008 | 5.2 | 37% | 32% |

Another issue is whether the various embodiments of nebulizers will generate aerosol size distributions that are similar to the OSHA-approved manual QLFT aerosol generator 20. One indicia of the size distribution is the normalized number concentration of an aerosol (dN/d log Dp, in units of counts/cc) measured as a function of the aerodynamic diameter of the aerosol. The dN/d log Dp parameter, also referred to as "normalized number concentration," comprises the number of particles or aerosol droplets contained within an aerodynamic diameter interval normalized against the size or "bin width" of the interval. The normalization enables comparison of distributions having different bin widths. To count the total number of particles within a size range, one adds the normalized number concentrations within the size range and multiplies it by the d log Dp (bin width).

Figure 22:
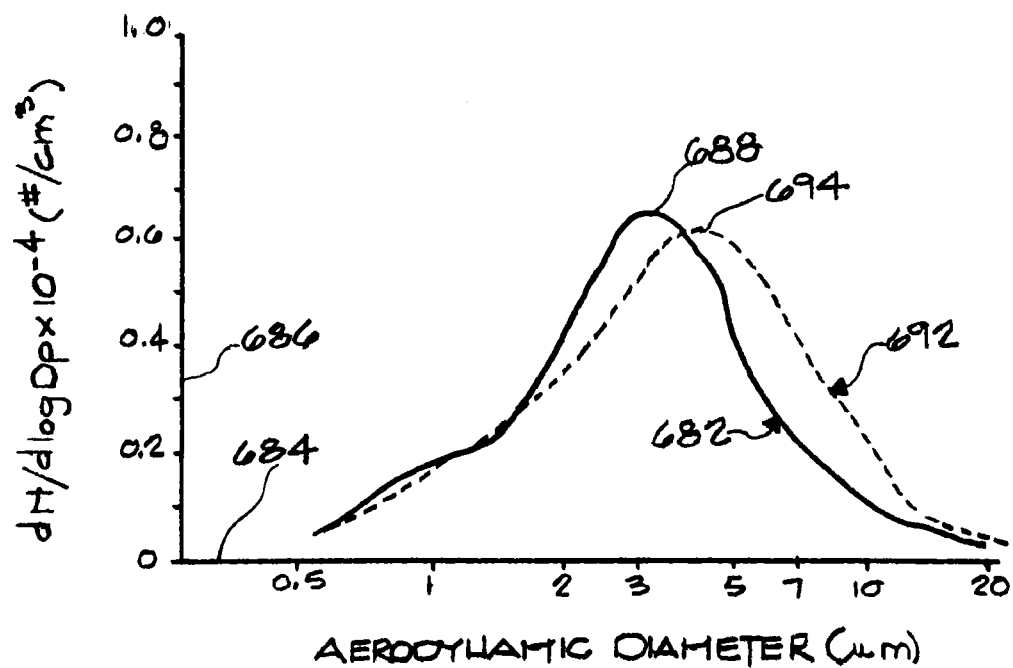
FIG. 22 is a semi-log graph comparing a representative size distribution generated by the QLFT aerosol generator of FIG. 1 vs. the QLFT of FIG. 2 implementing saccharin aerosol solutions.
Figure 23:
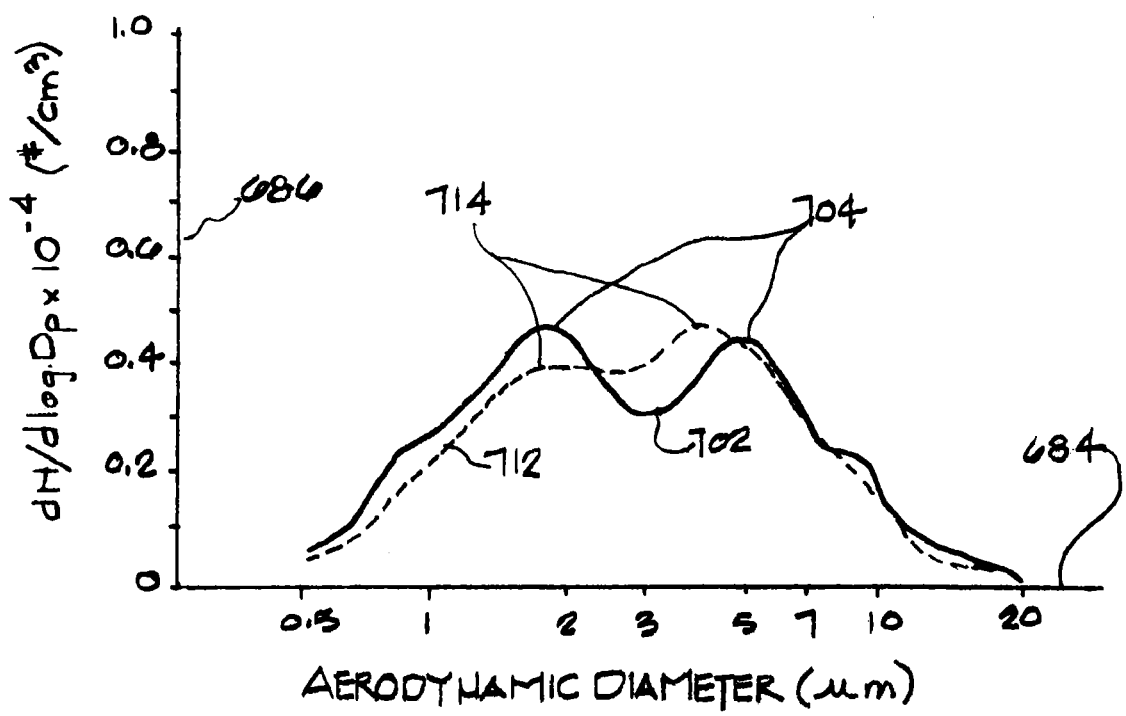
FIG. 23 is a semi-log graph comparing a representative size distribution generated by the QLFT aerosol generator of FIG. 1 vs. the QLFT of FIG. 2 implementing BITREX aerosol solutions.

Referring to FIGS. 22 and 23, data are presented comparing measured size distributions of the manual QLFT aerosol generator 20 and the automated QLFT generator 50 (FIG. 2). The size distribution measurements were performed with a TSI 3321 Aerodynamic Particle Sizer. Aerosol solutions comprising saccharin and BITREX were utilized in separate tests.

A manually generated saccharin size distribution 682 (that is, a size distribution generated with the manual QLFT aerosol generator 20 containing saccharin) is depicted in FIG. 22, where the distribution 682 is presented in a relationship graphing an aerodynamic diameter 684 in micrometers vs. a normalized number concentration 686 (counts/cc). The manually generated saccharin size distribution 682 is characterized by a maximum 688 at an aerodynamic diameter 84 of about 3.2 μm, where the normalized number concentration 686 is about 6500 counts/cc.

An auto-generated saccharin size distribution 692 (that is, a size distribution generated with the automated QLFT aerosol generator 50 containing saccharin) is also depicted in FIG. 22. The size distribution 692 has a maximum 694 at an aerodynamic diameter 684 of about 4.1 μM, where the normalized number concentration 686 is about 6000 counts/cc.

A manually generated BITREX size distribution 702 and an auto-generated BITREX size distribution 712 are presented in FIG. 23. The manually generated BITREX size distribution 702 is characterized by two local maxima 704 at aerodynamic diameters 684 of about 1.7 μm and 4.7 μm, where the normalized number concentrations 686 are approximately 4600 and 4400 counts/cc, respectively. The auto-generated BITREX size distribution 712 is also characterized by two local maxima 714 at aerodynamic diameters 684 of about 2.0 μm and 4.1 μm, where the normalized number concentration 686 are approximately 4200 and 4800 counts/cc, respectively.

The measured maximum/maxima 694, 714 of the size distributions of the automated QLFT generator 50 are within 1 μm with the measured maximum/maxima 688, 704 of the manual QLFT aerosol generator 20. This is within the ±3-μm non-repeatability of the DEVILBISS 40. Likewise, the concentration levels at the various maximum/maxima also compare favorably between the automated and manual units, being typically with ±10% of each other, also within the ±36% non-repeatability of the DEVILBISS 40.

Figure 24:
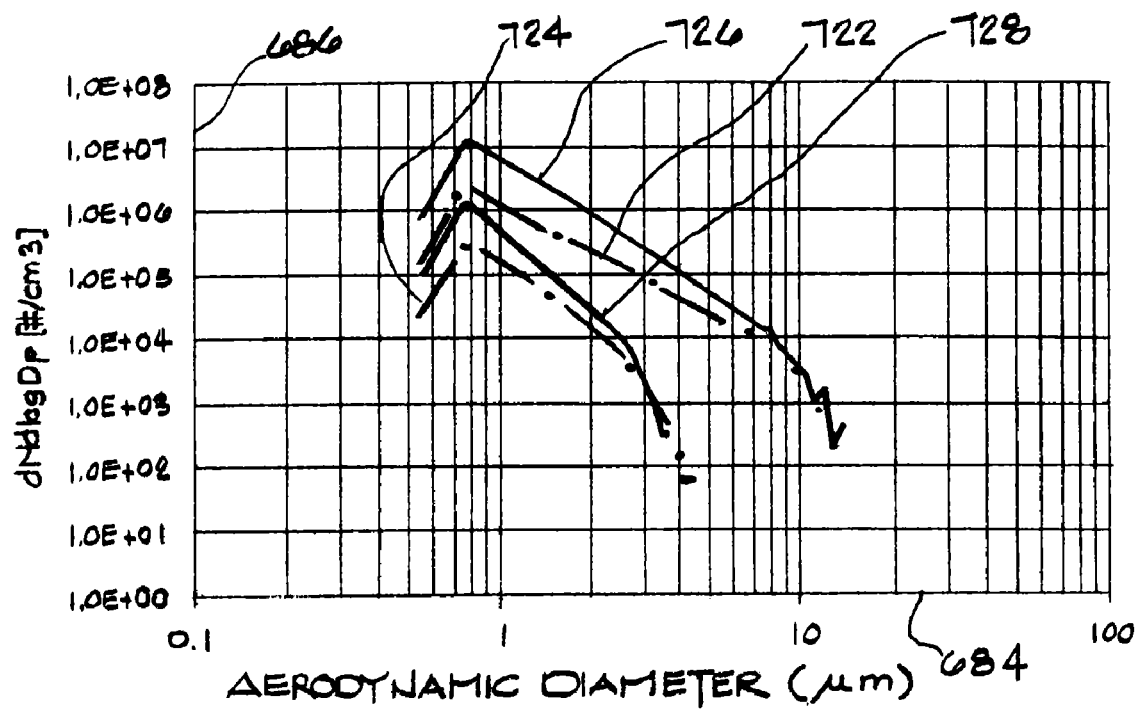
FIG. 24 is a log-log graph comparing a representative size distribution generated by the QLFT aerosol generator of FIG. 1 vs. the QLFT of FIG. 13 implementing saccharin aerosol solutions.
Figure 25:
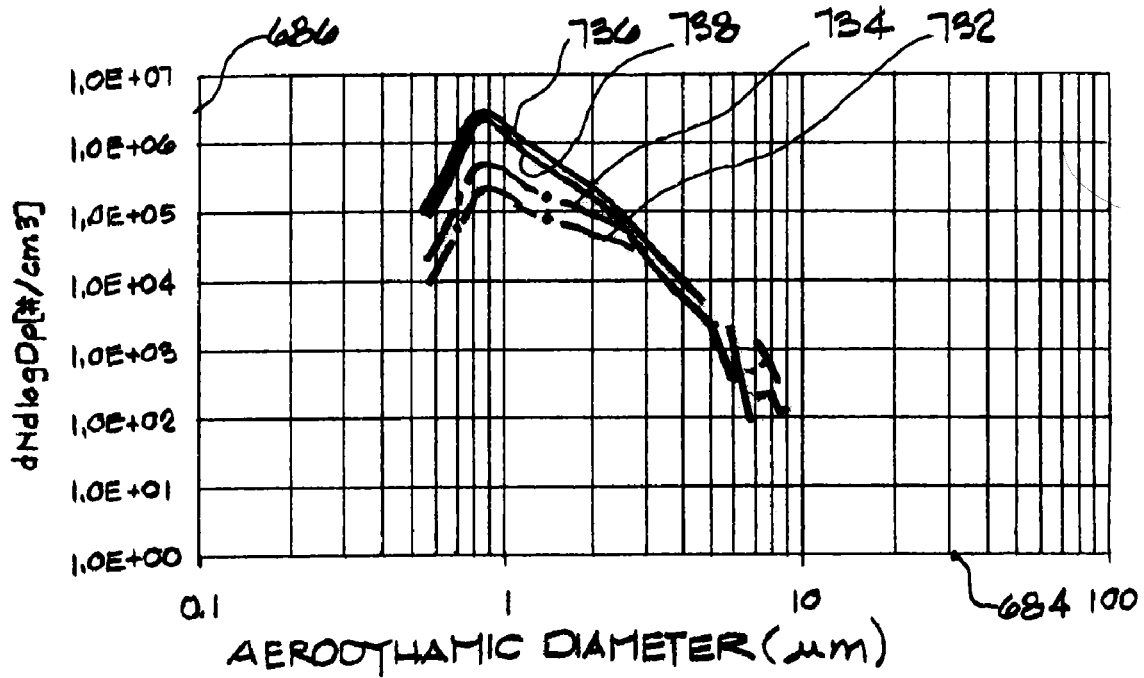
FIG. 25 is a log-log graph comparing a representative size distribution generated by the QLFT aerosol generator of FIG. 1 vs. the QLFT of FIG. 13 implementing BITREX aerosol solutions.

Referring to FIGS. 24 and 25, size distributions for the nebulizer unit 380 and the FT-13 were also obtained and compared in a separate test. In this test, the aerosol was run through a pair of diluters (TSI Model 3302A) to enable characterization of the aerosol concentration with an aerodynamic particle sizer (TSI APS) without clogging the aerodynamic particle sizer.

Size distributions 722 and 724 were obtained with the FT-13 using the fit and sensitivity saccharin aerosol solutions, respectively (FIG. 24). Size distributions 726 and 728 were obtained with the automated QLFT generator 370 implementing the nebulizer unit 380, again using the fit and sensitivity saccharin aerosol solutions, respectively.

Likewise, size distributions 732 and 734 were obtained with the FT-13 using the fit and sensitivity BITREX aerosol solutions, respectively (FIG. 25). Size distributions 736 and 738 were obtained with the automated QLFT generator 370 implementing the nebulizer unit 380, again using the fit and sensitivity BITREX aerosol solutions, respectively.

The routing of the aerosol stream through a pair of the diluters altered the profile of the size distributions vis-à-vis the size distributions presented in FIGS. 22 and 23. However, the contours of the size distributions produced by the FT-13 and the nebulizer unit 380 are in substantial agreement, having peak outputs near 0.8 μm. It is noted that the magnitudes of the various size distributions produced by the nebulizer unit 380 (e.g., 726, 728) can be adjusted for closer correlation with the magnitudes of the size distributions of the FT-13 (e.g., 722, 724) by changing the operating time of the automated QLFT generator 370. Such was the object of the mass dose tests executed with the test setup 650.

An indication of how well size distributions correlate is to compare the median diameters of the distribution, which are independent of the absolute magnitudes of the size distribution. Accordingly, the median diameters of the aerosol size distributions of FIGS. 24 and 25 are presented in Table 2. Note that the maximum difference between the FT-13 and the nebulizer unit 380 is 0.1 μm.

TABLE 2

| | Median Diameter (μm) | |
|---|---|---|
| Aerosol Solution | ManualQLFT (mg/squeeze) | Automated QLFT (mg/second) |
| BITREX Fit | 1.02 | 0.92 |
| Saccharin Fit | 0.89 | 0.88 |
| BITREX Sensitivity | 1.00 | 1.06 |
| Saccharin Sensitivity | 0.87 | 0.83 |

Referring to FIGS. 26 and 27, flow diagrams of a threshold test sequence 750 and a fit test sequence 752 that may be programmed into the various automated QLFT generators is depicted in an embodiment of the invention. For example, various steps depicted in the sequences 750 and 752 may be programmed as instruction into the PROM 132 of the advanced QLFT aerosol generator 190, as discussed below.

In the threshold test sequence 750, the operator may execute an initiation sequence 758 by powering up the advanced QLFT aerosol generator 190 and actuating the threshold test button 194 on the advanced QLFT aerosol generator 190. Programmed instructions may then appear on the display 204 that prompts the operator to execute a number of manual pre-test tasks 760. Such pre-test tasks 760 may include essentially a pre-test checklist of items such as making sure the right solutions is loaded in the nebulizer, that the testee is not to wear a mask, that the hood is in place on the testee, and/or that the nebulizer is hooked up to the hood. The pre-test tasks may also include entering the type of threshold solution being used (e.g., sweet or bitter). Acknowledgement by the operator that one or more of the pre-test tasks 760 has been executed may be entered through one or more of the keys on the operator console 192, such as the threshold test and taste acknowledge buttons 194 and 198 positioned immediately below the display 204. The display 204 may be programmed to indicate temporary reassignment of the buttons 194 and 198 (e.g., "sweet" and "bitter"), and the result stored in the RAM 208.

The threshold test sequence 750 may enter an automated generation phase 762. The automated generation phase may enter a dose determination loop 764 that includes executing a dose delivery sequence 766 to the testee, prompts the operator to inquire whether the testee tastes the threshold solution, and enters an input wait mode 768 for the operator to enter the response of the testee. If the response of the testee is positive, the threshold test sequence 750 exits the dose determination loop 764. If the response is negative, the advanced QLFT aerosol generator 190 may increment a counter that tracks how many negative responses the testee has indicated and check the total of the counter at 770. If the count at 770 exceeds a certain number (e.g., three, as used in the OSHA protocol), the threshold test sequence 750 may exit the dose determination loop 764 and enter a termination mode 772 wherein a message is displayed on display 204 that the testee has failed the threshold test. Otherwise, the dose determination loop 764 continues.

When the automated generation phase 762 is exited with a positive test result, the threshold test sequence 750 may execute a recording step 776 wherein the number of doses that were administered in the automated generation phase 762 (hereinafter "dose count") to elicit the positive response from the testee. The result may be displayed and/or may be recorded in the RAM 208. The threshold test sequence 750 may include a post-test phase 778 wherein the operator is instructed to perform post-test tasks such as cleaning the nebulizer.

The fit test sequence 752 (FIG. 27) may include an initiation sequence 792 that is initiated upon actuation of the fit test button 196, followed by prompting to execute a number of pre-test tasks 794. The pre-test tasks 794 may be generally the same as the pre-test tasks 760 of the threshold test sequence 750. One exception would be that the pre-test tasks 794 of the fit test sequence 752, unlike the pre-test tasks 760 of the threshold test sequence 750, would prompt the operator to make sure the mask to be tested is properly fitted on the testee. In addition, the routine may recall from the RAM 208 the type solution used in the threshold test sequence and instruct, rather than inquire, the type of solution to use in the fit test.

The fit test sequence 752 may enter an automated generation phase 796 that includes an initial pre-exercise dose delivery routine 810 that delivers a dose of fit test solution based on the dose count established during the threshold test. That is, the greater the dose count, the greater the mass dose delivered during execution of the initial pre-exercise dose delivery routine 810. The mass dose administered by the pre-exercise dose delivery routine 810 may be manually entered by the operator (e.g., by pressing a designated button on the operator console 192 a number of times that corresponds with the dose count), or alternatively may be read from the RAM 208 as stored during the threshold test sequence 750.

The fit test sequence 752 may then enter a repeat exercise loop 800. The operator may be prompted at 820 to instruct the testee to perform an appropriate exercise for 60 seconds. After the testee performs the exercise, a post-exercise delivery routine 830 may be executed that delivers substantially half of the mass dose administered during the initial pre-exercise dose delivery routine 810, thus substantively simulating the OSHA protocol for testing with manual nebulizers. The repeat exercise loop 800 may then prompt the operator to inquire whether the testee tastes the fit test solution, and enter an input wait mode 832 for the operator to enter the response of the testee. If the response from the testee is negative (no taste), the repeat exercise loop 800 continues on to the next test.

If the testee performs all of the OSHA-specified exercises without tasting the fit test solution, the repeat exercise loop is terminated at 834 and a message may be displayed indicating that the QLFT test is passed. If at any time the testee indicates tasting the fit test solution at 832, the repeat exercise loop is terminated at 836 and a message may be displayed indicating that the QLFT test is failed.

Currently, there are a total of seven exercises to be performed by the testee in the OSHA protocol. The fit test sequence 752 may be modified to include more or less exercises should the OSHA protocol change, or if a protocol from a source other than OSHA is desired. Likewise, other parameters (e.g. time delays, dosages, instructions to perform manual tasks) of the fit test sequence 752 may be altered to accommodate changes or substitutions to the OSHA protocol.

The dose delivery sequences 766, 810 and 830 may be pre-programmed into the advanced QLFT aerosol generator 190 to activate the air pump 58 for a specific interval of time that is in accordance with calibration data such as presented in Table 1. The duration of the time interval will generally be a function of the mass dose to be delivered, and can also be a function of the type of fit test solution being utilized. That is, the delivery sequences 766, 810 and 830 may access equivalent run times for a single manually-delivered dose (such as presented in Table 1) that are stored in the RAM 208 or PROM 132, and multiply that tailored dose by the dose count to affect an accurate mass dose delivery. Alternatively, the equivalent run time may be a fixed value that is a numerical average of the various equivalent run times; such an approach may result in less accurate mass dose delivery, but still be sufficient to substantially meet OSHA protocols.

While certain portions of the discussion above are directed to operation of the advanced QLFT aerosol generator 190, it is understood that any of the various embodiments that include microprocessor-readable instructions may be programmed similarly.

It is also noted that while the instant disclosure is directed to meeting OSHA requirements and protocol, other protocols may also be implemented using the methods and apparatuses disclosed herein, still being within the spirit and scope of the invention.

The invention is amenable to various modifications and alternative forms. Specifics thereof have been presented by way of example embodiments depicted and described. It is understood that the intention of the embodiments of the invention presented herein is not to limit the invention to the particular embodiments described. Rather, the intention is to cover all modifications, equivalents, and alternatives falling within the spirit and scope of the invention as defined by the appended claims.

Accordingly, each of the features and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "steps for" are recited in the subject claim.

What is claimed is:

1. A qualitative fit tester comprising:

a nebulizer base operatively coupled with a removable cartridge, said removable cartridge including an upper portion, a side portion and a lower portion that defines an interior chamber for containment of a solution, said upper portion forming a closure over said side and lower portions, said removable cartridge having structure that defines at least one vent hole in fluid communication with said interior chamber;

an aspirator nozzle for production of an aspirator jet that defines a jet axis, said aspirator nozzle being coupled to or integral with said nebulizer base; said upper portion including a structure that at least partially defines a flow passage, said flow passage establishing fluid communication between said interior chamber of said removable cartridge and a zone proximate said jet axis; an upper housing extending from one of said nebulizer base and said removable cartridge, said upper housing including an exhaust port; and a tripping structure located downstream of said aspirator nozzle for intersection of at least a portion of said aspirator jet, such that when a gas flow is introduced through said aspirator nozzle, said solution is drawn from said removable cartridge through said flow passage and entrained in said aspirator jet, said aspirator jet impacting said tripping structure to atomize and convey at least a portion of said solution entrained therein to exit said exhaust port, said portion of said solution that exits said exhaust port being suitable for qualitative fit testing; wherein said removable cartridge includes a catch basin for collection of a remaining portion of said solution, said catch basin being in fluid communication with at least one of said at least one vent hole for return of said remaining portion of said solution to said interior chamber of said removable cartridge.

2. The qualitative fit tester of claim 1 wherein said removable cartridge is one of disposed within and coupled directly to said upper housing, said upper housing being removable for access to and placement of said removable cartridge.

3. The qualitative fit tester of claim 2 wherein said removable cartridge and said upper housing include structures that cooperate for capture of said remaining portion of said solution that is entrained in said aspirator jet that does not exit said exhaust port, said remaining portion being returned to said interior chamber of said removable cartridge.

4. The qualitative fit tester of claim 2 wherein said removable cartridge, said structure defining a flow passage and said tripping structure are integral.

5. The qualitative fit tester of claim 2 wherein:

said tripping structure is joined to or integral with said upper housing; and said aspirator nozzle is joined to or integral with said removable cartridge.

6. The qualitative fit tester of claim 2 wherein said tripping structure and said aspirator nozzle are joined to or integral with said removable cartridge.

7. The qualitative fit tester of claim 2 wherein:

said tripping structure is joined to or integral with said upper housing; and at least a portion of said aspirator nozzle is joined to or integral with said tripping structure.

8. The qualitative fit tester of claim 1 wherein said nebulizer base comprises a hand-held console box and a pressure source operatively coupled with said aspirator nozzle for selective generation of said gas flow through said aspirator nozzle.

9. The qualitative fit tester of claim 8 wherein said pressure source comprises an air pump driven by an electric motor, said air pump and motor being disposed within said hand-held console box.

10. The qualitative fit tester of claim 8 further comprising a microprocessor operatively coupled with a memory device, control circuitry and an operator console, said control circuitry being operatively coupled with said pressure source for control of said gas flow from said pressure source with said microprocessor, said microprocessor, control circuitry and memory device being disposed within said hand-held console box, said memory device including microprocessor-readable instructions, said instructions comprising:

receiving an input from said operator console;

activating said gas flow between said pressure source and said aspirator nozzle for a first predetermined time interval, said first predetermined time interval being selectively determined based on said input from said operator console;

terminating said gas flow between said pressure source and said aspirator nozzle established in the step of activating for a second predetermined time interval, said second predetermined time interval being selectively determined based on said input from said operator console; and repeating said steps of activating and terminating at least once.

11. The qualitative fit tester of claim 10 further comprising a heater operatively coupled with said removable cartridge and said control circuitry, and wherein said memory device includes microprocessor-readable instructions for energizing said heater.

12. The qualitative fit tester of claim 1 further comprising a heater operatively coupled with said removable cartridge.

13. The qualitative fit tester of claim 1 wherein said removable cartridge comprises a lower portion and an upper portion, said lower portion including structure that defines said aspirator nozzle, said structure defining said flow passage comprising a channel on one of said aspirator nozzle and said upper portion of said removable cartridge that cooperates with the other of said aspirator nozzle and said upper portion of said removable cartridge to define said flow passage.

14. The qualitative fit tester of claim 1 wherein said structure defining said flow passage includes a head having an exit orifice.

15. The qualitative fit tester of claim 1 further comprising a random access memory and an input/output communication device operatively coupled to said microprocessor for transfer of data to and from said memory device and said random access memory.

16. The qualitative fit tester of claim 15 wherein said input/output communication device is wireless.

17. The qualitative fit tester of claim 1, wherein said flow passage is a bypass channel.

* * * * *